US 8,987,291 B2

(12) United States Patent
Evenstad et al.

(10) Patent No.: US 8,987,291 B2
(45) Date of Patent: *Mar. 24, 2015

(54) OPIOID-CONTAINING ORAL PHARMACEUTICAL COMPOSITIONS AND METHODS

(71) Applicant: Upsher-Smith Laboratories, Inc., Maple Grove, MN (US)

(72) Inventors: Kenneth L. Evenstad, Naples, FL (US); Christian F. Wertz, St. Louis Park, MN (US); James S. Jensen, Edina, MN (US); Victoria Ann O'Neill, Wayzata, MN (US); Stephen M. Berge, Shoreview, MN (US)

(73) Assignee: Upsher Smith Laboratories, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/715,432

(22) Filed: Dec. 14, 2012

(65) Prior Publication Data

US 2013/0123293 A1 May 16, 2013

Related U.S. Application Data

(63) Continuation of application No. 13/142,784, filed as application No. PCT/US2009/069902 on Dec. 31, 2009, now Pat. No. 8,362,029.

(60) Provisional application No. 61/141,765, filed on Dec. 31, 2008.

(51) Int. Cl.
| | | |
|---|---|---|
| A01N 43/42 | (2006.01) | |
| A61K 31/44 | (2006.01) | |
| A01N 33/02 | (2006.01) | |
| A61K 31/135 | (2006.01) | |
| A61K 31/439 | (2006.01) | |
| A61K 31/10 | (2006.01) | |
| A61K 9/20 | (2006.01) | |
| A61K 31/19 | (2006.01) | |
| A61K 31/485 | (2006.01) | |
| A61K 31/192 | (2006.01) | |

(52) U.S. Cl.
CPC ............... *A61K 31/439* (2013.01); *A61K 31/10* (2013.01); *A61K 9/2013* (2013.01); *A61K 9/2054* (2013.01); *A61K 31/19* (2013.01); *A61K 31/485* (2013.01); *A61K 31/135* (2013.01); *A61K 31/192* (2013.01)
USPC .......................................... 514/282; 514/650

(58) Field of Classification Search
None
See application file for complete search history.

(56) References Cited

U.S. PATENT DOCUMENTS

| | | | |
|---|---|---|---|
| 4,834,965 | A | 5/1989 | Martani et al. |
| 5,206,262 | A | 4/1993 | Donati et al. |
| 5,330,766 | A | 7/1994 | Morella et al. |
| 5,368,852 | A | 11/1994 | Umemoto et al. |
| 5,378,474 | A | 1/1995 | Morella et al. |
| 5,580,578 | A | 12/1996 | Oshlack et al. |
| 5,639,476 | A | 6/1997 | Oshlack et al. |
| 5,914,129 | A | 6/1999 | Mauskop |
| 5,958,452 | A | 9/1999 | Oshlack et al. |
| 5,958,459 | A | 9/1999 | Chasin et al. |
| 5,965,161 | A | 10/1999 | Oshlack et al. |
| 5,968,551 | A | 10/1999 | Oshlack et al. |
| 6,068,855 | A | 5/2000 | Leslie et al. |
| 6,127,352 | A | 10/2000 | Uribe |
| 6,143,353 | A | 11/2000 | Oshlack et al. |
| 6,261,599 | B1 | 7/2001 | Oshlack et al. |
| 6,294,195 | B1 | 9/2001 | Oshlack et al. |
| 6,335,033 | B2 | 1/2002 | Oshlack et al. |
| 6,696,066 | B2 | 2/2004 | Kaiko et al. |
| 6,696,088 | B2 | 2/2004 | Oshlack et al. |
| 6,699,502 | B1 | 3/2004 | Fanara et al. |
| 6,706,281 | B2 | 3/2004 | Oshlack et al. |
| 6,733,783 | B2 | 5/2004 | Oshlack et al. |
| 6,743,442 | B2 | 6/2004 | Oshlack et al. |
| 6,902,742 | B2 | 6/2005 | Devane et al. |
| 6,905,709 | B2 | 6/2005 | Oshlack et al. |
| 7,070,806 | B2 | 7/2006 | Oshlack et al. |
| 7,083,807 | B2 | 8/2006 | Fanara et al. |
| 7,172,767 | B2 | 2/2007 | Kaiko et al. |
| 7,192,966 | B2 | 3/2007 | Mayo-Alvarez et al. |
| 7,201,920 | B2 | 4/2007 | Kumar et al. |
| 7,794,750 | B2 | 9/2010 | Naringrekar et al. |
| 7,906,141 | B2 | 3/2011 | Ziegler et al. |
| 2002/0058050 | A1 | 5/2002 | Sackler et al. |

(Continued)

FOREIGN PATENT DOCUMENTS

| | | |
|---|---|---|
| DE | 37 37 154 A1 | 7/1988 |
| DE | 199 40 944 A1 | 3/2001 |

(Continued)

OTHER PUBLICATIONS

"Aerosol® OT surfactants" datasheet, Cytec Industries, Inc., West Paterson, NJ, copyright 2000; 6 pgs.

(Continued)

*Primary Examiner* — James D Anderson
*Assistant Examiner* — William Lee
(74) *Attorney, Agent, or Firm* — Mueting Raasch & Gebhardt, P.A.

(57) ABSTRACT

The present invention provides sustained-release oral pharmaceutical compositions and methods of use. The sustained-release oral pharmaceutical compositions include an opioid (including salts thereof) and a salt of a non-steroidal anti-inflammatory drug (NSAID).

20 Claims, 3 Drawing Sheets

(56) References Cited

U.S. PATENT DOCUMENTS

| | | |
|---|---|---|
| 2002/0176888 A1 | 11/2002 | Bartholomaeus et al. |
| 2003/0035837 A1 | 2/2003 | Sackler et al. |
| 2003/0044464 A1 | 3/2003 | Ziegler et al. |
| 2003/0049317 A1 | 3/2003 | Lindsay |
| 2003/0049318 A1 | 3/2003 | Davis et al. |
| 2003/0065002 A1 | 4/2003 | Caruso et al. |
| 2003/0068375 A1 | 4/2003 | Wright et al. |
| 2003/0092724 A1 | 5/2003 | Kao et al. |
| 2004/0062812 A1 | 4/2004 | Maloney |
| 2004/0224020 A1 | 11/2004 | Schoenhard |
| 2004/0266807 A1 | 12/2004 | Oshlack et al. |
| 2005/0020613 A1 | 1/2005 | Boehm et al. |
| 2005/0074493 A1 | 4/2005 | Mehta et al. |
| 2005/0080012 A1 | 4/2005 | Mickle et al. |
| 2005/0123606 A1 | 6/2005 | Kidane |
| 2005/0158382 A1 | 7/2005 | Cruz et al. |
| 2005/0169990 A1 | 8/2005 | Kao et al. |
| 2005/0191343 A1 | 9/2005 | Liang |
| 2005/0245483 A1 | 11/2005 | Brogmann et al. |
| 2006/0003008 A1 | 1/2006 | Gibson et al. |
| 2006/0034872 A1 | 2/2006 | Woolf |
| 2006/0083690 A1 | 4/2006 | Chang |
| 2006/0110327 A1 | 5/2006 | Emigh et al. |
| 2006/0177380 A1 | 8/2006 | Emigh et al. |
| 2006/0210625 A1 | 9/2006 | Kidane |
| 2006/0251721 A1 | 11/2006 | Cruz et al. |
| 2006/0286174 A1 | 12/2006 | Raman et al. |
| 2007/0020339 A1 | 1/2007 | Bear |
| 2007/0142421 A1 | 6/2007 | Mayo-Alvarez et al. |
| 2007/0281016 A1 | 12/2007 | Kao et al. |
| 2007/0281018 A1 | 12/2007 | Qiu et al. |
| 2008/0008659 A1 | 1/2008 | Guimberteau et al. |
| 2008/0014228 A1 | 1/2008 | Darmuzey et al. |
| 2008/0031901 A1 | 2/2008 | Qiu et al. |
| 2009/0214648 A1 | 8/2009 | Kandakatla et al. |
| 2009/0264454 A1* | 10/2009 | Nickell .................. 514/282 |

FOREIGN PATENT DOCUMENTS

| | | | |
|---|---|---|---|
| DE | 10023699 A1 | 4/2001 | |
| EP | 0 009 808 A1 | 4/1980 | |
| EP | 0 546 676 A1 | 6/1993 | |
| EP | 0 649 657 A1 | 4/1995 | |
| EP | 1 293 195 A1 | 3/2003 | |
| EP | 1 384 471 A1 | 1/2004 | |
| EP | 2 074 990 A1 | 7/2009 | |
| EP | 2 085 076 A1 | 8/2009 | |
| WO | WO 00/04879 A1 | 2/2000 | |
| WO | 01/15667 A1 | 8/2001 | |
| WO | 2007/022356 A2 | 2/2007 | |
| WO | WO 2011/034554 A1 | 3/2011 | |

OTHER PUBLICATIONS

Ahmed et al. "In vitro release kinetics study of naproxen from swellable hydrophilic matrix tablets." *Bangladesh Phar Journal.* 2010; 13:18-22.

Baveja et al. "Influence of surfactants on drug release from hydroxypropylmethylcellulose matrices." *Int. J Pharmaceutics.* 1988; 41:83-90.

Bhatt et al., "Saccharin as a salt former. Enhanced solubilities of saccharinates of active pharmaceutical ingredients," *Chem. Commun.* 2005:1073-1075.

Bravo et al. "In-vitro studies of diclofenac sodium controlled-release from biopolymeric hydrophilic matrices." *J. Pharm. Pharmaceut. Sci.* 2002; 5:213-219.

Carlson et al., "The Plasma Pharmacokinetics of R-(+)-Lipoic Acid Administered as Sodium (R)-(+)-Lipoate to Healthy Human Subjects," *Alternative Medicine Review*, 2007; 12(4):343-351.

Choulis et al., "Factors Effecting Drug Release From Inert Matrices. Part 1: Effects of Surfactants on the Release of Quinine Sulfate," *Pharmazie*, Apr. 1975; 30(4):233-236.

Christie et al., "Opioids, NSAIDs and 5-lipoxygenase inhibitors act synergistically in brain via arachidonic acid metabolism," *Inflammation Research*, Jan. 1999; 48(1):1-4.

Daly et al., "The effect of anionic surfactants on the release of chlorpheniramine from a polymer matrix tablet," *Int. J. Pharmaceutics*, 1984; 18(1-2):201-205.

Davis et al., "The use of gamma scintigraphy to simultaneously monitor the in vivo dissolution of drug from two formulations," *J. Pharmacy & Pharmacology*, Dec. 1983; 35(Suppl.): 105P.

El-Laithy, "Preparation and Physicochemical Characterization of Dioctyl Sodium Sulfosuccinate (Aerosol OT) Microemulsion for Oral Drug Delivery," *AAPS PharmSciTech*, Mar. 31, 2003; 4(1):Article 11; 10 pgs.

Feely et al., "Influence of surfactants on drug release from hydroxypropylmethylcellulose matrices," *Int. J. Pharmaceutics*, Jan. 1988; 41(1-2):83-90.

Ferrero et al. "Towards elucidation of the drug release mechanism from compressed hydrophilic matrices made of cellulose ethers. I. Pulse-field-gradient spin-echo NMR study of sodium salicylate diffusivity in swollen hydrogels with respect to polymer matrix physical structure." *J. Controlled Release.* 2008; 128:71-79.

Ferrero Rodriguez et al. "Hydrophilic cellulose derivatives as drug delivery carriers. Influence of substitution type on the properties of compressed matrix tablets." In *Handbook of Pharmaceutical Controlled Release Technology* (ed. Donald L. Wise). CRC Press. 2000. 1:1-30.

Fingl et al., "General Principles," Chapter 1, *The Pharmacological Basis of Therapeutics*, New York, NY, 1975:1-46.

"Future Opioids. The Birth of a New Generation," [retrieved on Jun. 15, 2011]. Retrieved from the Internet: <URL:http://www.opiods.com>; 7 pgs.

Ghosh et al. "Drug Delivery Through Osmotic Systems—An Overview." *J. App. Pharma Science.* 2011; 01(02):38-49.

International Search Report and Written Opinion issued Nov. 25, 2010, by the European Patent Office, Patent Application No. PCT/US2009/069912.

International Search Report and Written Opinion issued Jul. 9, 2010, by the European Patent Office, Patent Application No. PCT/US2009/069902.

Kamel et al. "Pharmaceutical significance of cellulose: a review." *eXPRESS Polymer Letters.* 2008; 2:758-778.

Levina et al., "The Influence of Excipients on Drug Release from Hydroxypropyl Methylcellulose Matrices," *J. Pharmaceutical Sci.*, Nov. 2004; 93(11):2746-2754.

Matschiner et al., "Characterization of ion pair formation between erythromycin and lipophilic counter ions," *Pharmazie*, 1995; 50(7):462-464.

Pygall et al., "Mechanisms of drug release in citrate buffered HPMC matrices," *Int. J. Pharmaceutics*, 2009; 370:110-120.

Raffa, "Pharmacology of oral combination analgesics: rational therapy for pain," *J. Clin. Pharm. Ther.*, Aug. 2001; 26(4):257-264.

Rao et al., "Effect of Sodium Lauryl Sulfate on the Release of Rifampicin from Guar Gum Matrix," *Indian J. Pharmaceutical Sci.*, Sep.-Oct. 2000; 62(5):404-406.

Ranga Rao et al. "Cellulose matrices for zero-order release of soluble drugs." 1988. *Drug Dev. And Ind. Pharm.* 14:2299-2320.

Theeuwes et al., "Osmotic delivery systems for the β-adrenoceptor antagonists metoprolol and exprenolol: design and evaluation of systems for once-daily administration." 1985. *Br. J Clin. Pharmac.* 19:69S-76S.

Tiwari et al. "Controlled release formulation of tramadol hydrochloride using hydrophilic and hydrophobic matrix system." 2003. *AAPS PharmSciTech.* 4:1-6.

Wells et al., "Effect of anionic surfactants on the release of chlorpheniramine maleate from an inert, heterogeneous matrix," *Drug Development and Industrial Pharmacy*, 1992, 18(2):175-186.

Baveja et al. "Zero-order release hydrophilic matrix tablets of β-adrenergic blockers". 1987. *International Journal of Pharmaceutics.* 39:39-45.

* cited by examiner

Figure 1. Dissolution of TMD formulations in phosphate buffer
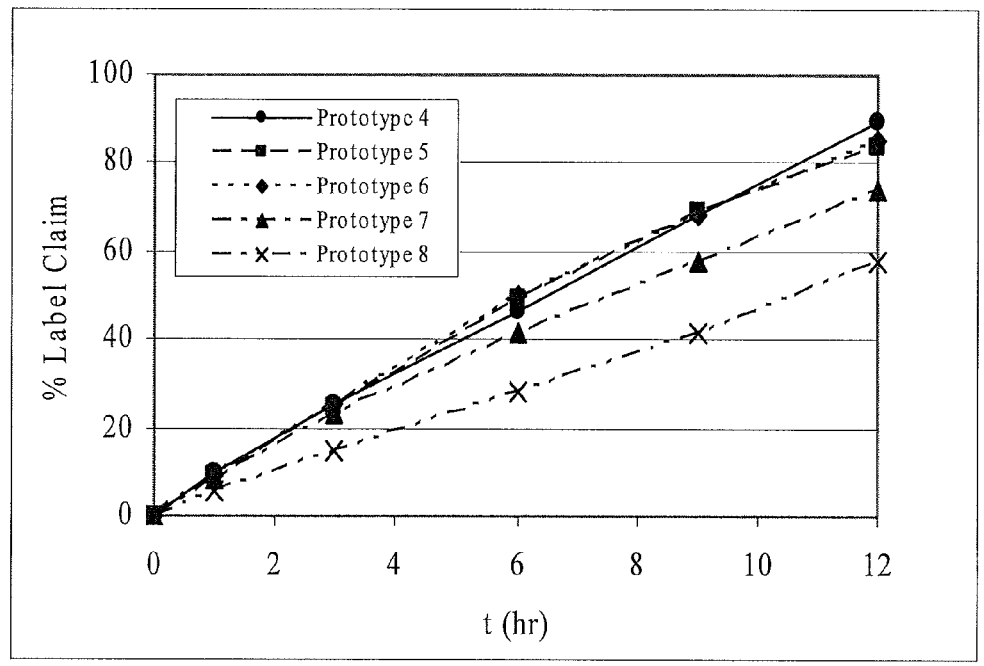
Figure 2. Dissolution of TMD formulations in phosphate buffer
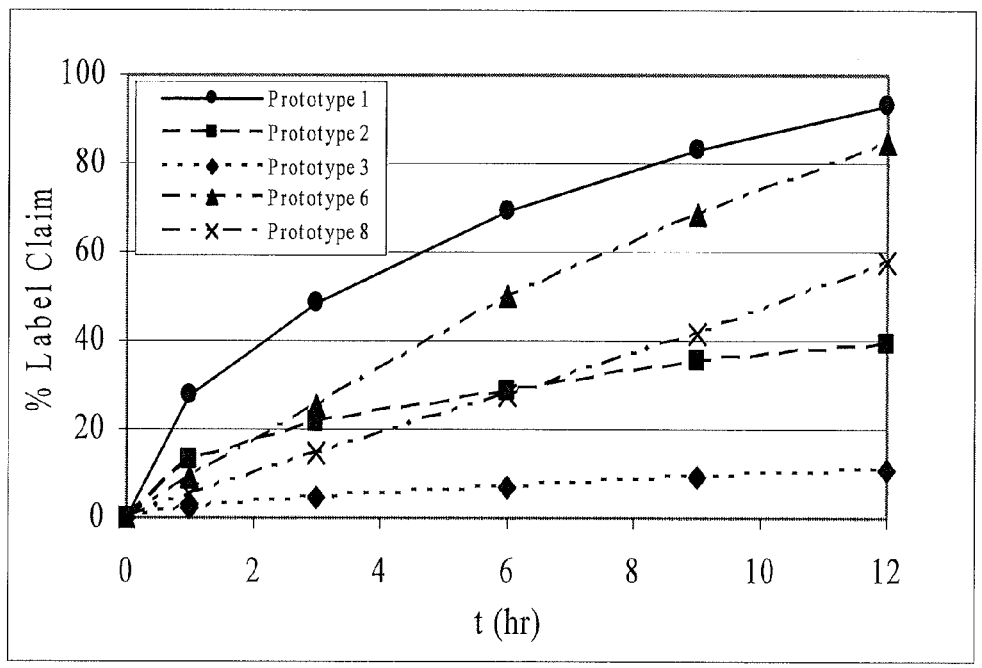

Figure 3. Dissolution of HCB formulations in phosphate buffer
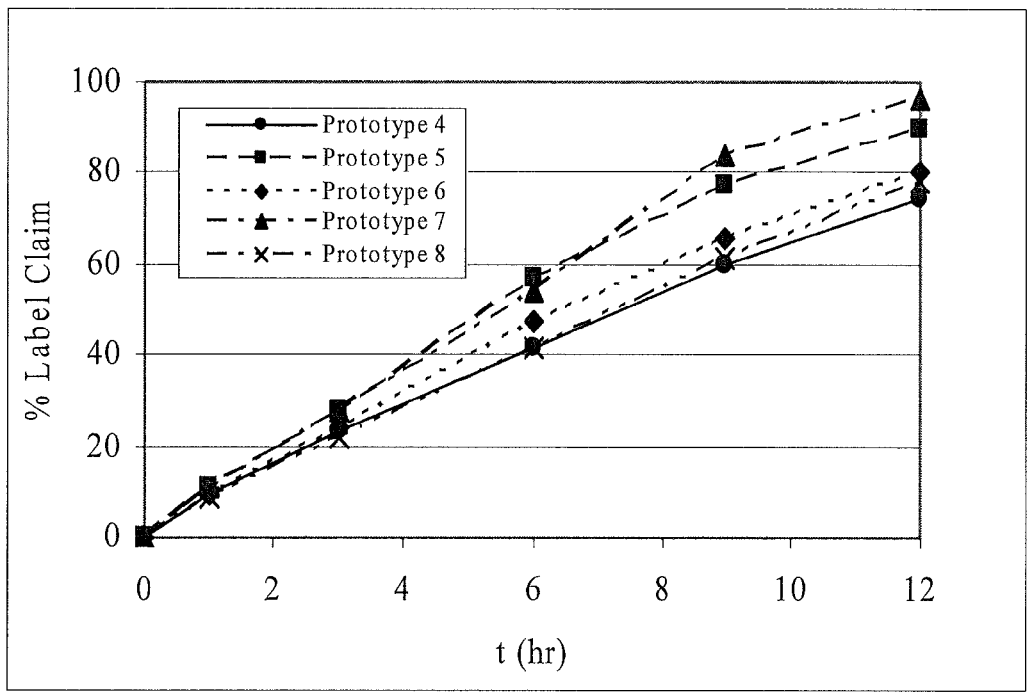
Figure 4. Dissolution of HCB formulations in phosphate buffer
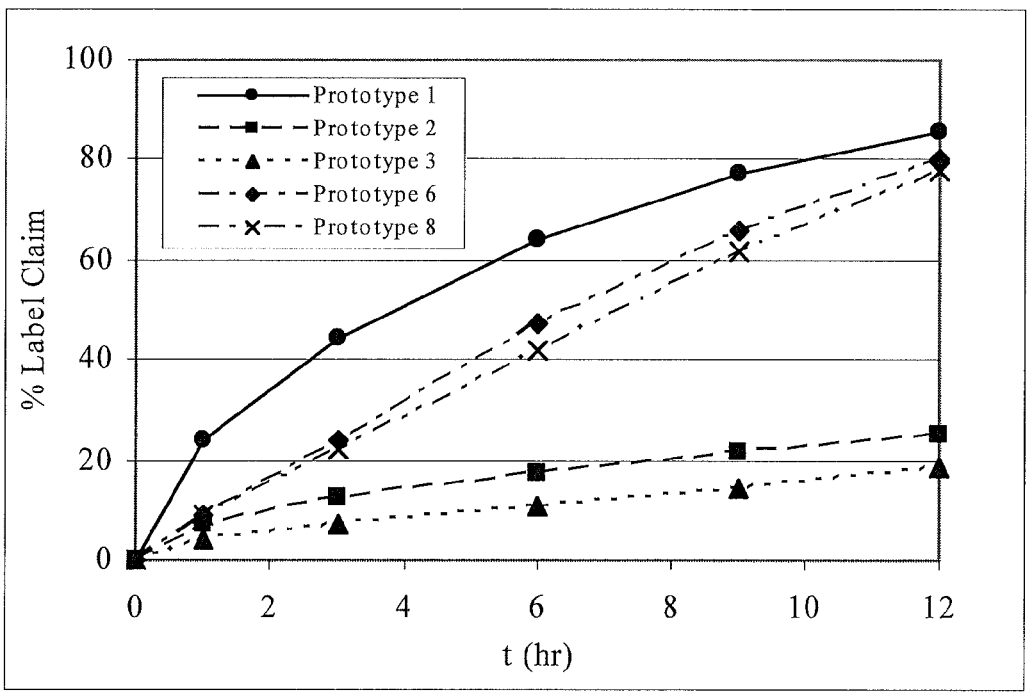

Figure 5. Dissolution of a DXM formulation (Prototype 1) in acidic and hydroalcoholic media
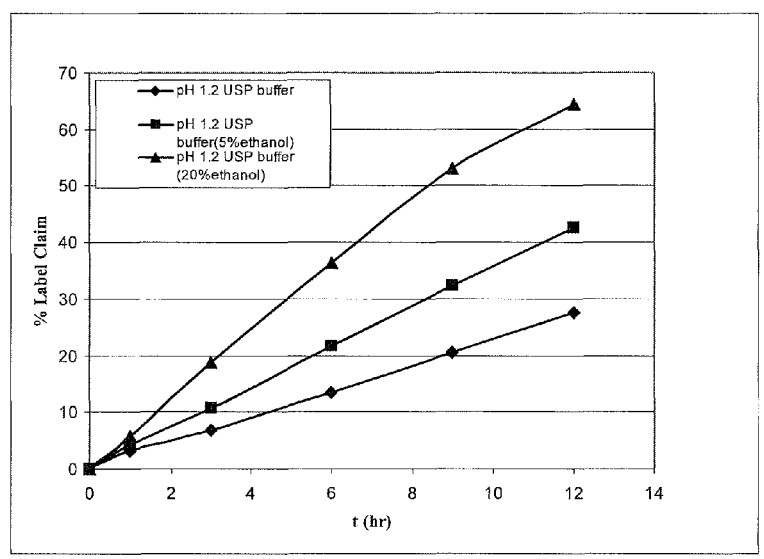

OPIOID-CONTAINING ORAL PHARMACEUTICAL COMPOSITIONS AND METHODS

CONTINUING AND RELATED APPLICATION DATA

This application is continuation of U.S. Ser. No. 13/142,784, which is a U.S. National Stage Application of International Application No. PCT/US2009/069902, filed on Dec. 31, 2009, published in the English language on Jul. 8, 2010 as International Publication No. WO 2010/078486 A2, which claims the benefit of U.S. Provisional Application Ser. No. 61/141,765, filed Dec. 31, 2008. Attention is also directed to International Application No. PCT/US2009/069912, filed Dec. 31, 2009, published in the English language on Mar. 24, 2011 as International Publication No. WO 2011/034554 A1, which claims the benefit of U.S. Provisional Application Ser. No. 61/243,391, filed Sep. 17, 2009. All of the above are incorporated by reference herein.

BACKGROUND

Chronic pain is a major contributor to disability in the industrialized world and is the cause of an untold amount of suffering. The successful treatment of severe and chronic pain is a primary goal of the physician, with opioid analgesics being the current drugs of choice.

Opioid analgesics (i.e., opioids' having analgesic properties) are drugs that function in a manner similar to that of morphine. These agents work by binding to opioid receptors, which are found principally in the central nervous system and the gastrointestinal tract. Although the term opiate is often used as a synonym for opioid, it is more frequently used to refer to the natural opium alkaloids and the semi-synthetics derived from them.

An important goal of analgesic therapy is to achieve continuous relief of chronic pain. Regular administration of an analgesic is generally required to ensure that the next dose is given before the effects of the previous dose have worn off. Compliance with opioids increases as the required dosing frequency decreases. Non-compliance results in suboptimal pain control and poor quality-of-life outcomes. Scheduled rather than "as needed" administration of opioids is currently recommended in guidelines for their use in treating chronic non-malignant pain. Unfortunately, evidence from prior clinical trials and clinical experience suggests that the short duration of action of immediate-release opioid formulations would necessitate 4-hourly administrations in order to maintain optimal levels of analgesia in patients with chronic pain. Moreover, immediate-release formulations can exhibit low oral bioavailability. Thus, there is a need for new opioid-containing oral pharmaceutical compositions that provide sustained release, and ideally zero-order release kinetics, and less frequent dosing.

Opioids (particularly those with analgesic activity) are sometimes the subject of abuse. Typically, a particular dose of an opioid analgesic is more potent when administered parenterally as compared to the same dose administered orally. Therefore, one popular mode of abuse of oral opioid formulations involves the extraction of the opioid from the dosage form, and the subsequent injection of the opioid (using any "suitable" vehicle for injection) in order to achieve a "high." Also, some formulations can be tampered with in order to provide the opioid contained therein better availability for illicit use. For example, an opioid-containing tablet can be crushed in order to render the opioid therein available for immediate release upon oral, nasal, or intravenous administration. An opioid formulation can also be abused by administration of more than the prescribed dose of the drug. Thus, there is a need for new opioid-containing oral pharmaceutical compositions that provide abuse deterrence in addition to providing sustained-release, ideally zero-order release kinetics, and less frequent dosing.

SUMMARY

The present invention provides sustained-release oral pharmaceutical compositions and methods of use.

In one embodiment, the present invention provides a sustained-release oral pharmaceutical composition comprising within a single dosage form: a hydrophilic matrix; a therapeutically effective amount of an opioid (including salts thereof); and a salt of a non-steroidal anti-inflammatory drug (NSAID); wherein the opioid (including salts thereof) and the salt of an NSAID are within the hydrophilic matrix; wherein the composition exhibits a release profile comprising a substantial portion that is representative of zero-order release kinetics (with respect to the opioid) under in vitro conditions.

In another embodiment, the present invention provides a sustained-release oral pharmaceutical composition comprising within a single dosage form: a hydrophilic matrix; a therapeutically effective amount of an opioid (including salts thereof); a salt of a non-steroidal anti-inflammatory drug (NSAID); and a pharmaceutically acceptable anionic surfactant; wherein the opioid (including salts thereof), the salt of an NSAID, and the anionic surfactant are within the hydrophilic matrix. Preferred such compositions exhibit a release profile comprising a substantial portion that is representative of zero-order release kinetics under in vitro conditions.

In certain embodiments, the opioid comprises a tertiary amine. In certain embodiments, the opioid comprises a ring nitrogen that is a tertiary amine.

In a preferred embodiment, the present invention provides a sustained-release oral pharmaceutical composition comprising within a single dosage form: a hydrophilic matrix; a therapeutically effective amount of an opioid selected from the group consisting of hydrocodone, tramadol, salts thereof, and combinations thereof; and a salt of a non-steroidal anti-inflammatory drug (NSAID) selected from the group consisting of a salt of naproxen, diclofenac, ibuprofen, and combinations thereof; wherein the opioid (including salts thereof) and the salt of an NSAID are within the hydrophilic matrix; wherein the composition has a release profile comprising a substantial portion that is representative of zero-order release kinetics under in vitro conditions.

In another preferred embodiment, the present invention provides a sustained-release oral pharmaceutical composition comprising within a single dosage form: a hydrophilic matrix; a therapeutically effective amount of an opioid selected from the group consisting of hydrocodone, tramadol, salts thereof, and combinations thereof; a salt of a non-steroidal anti-inflammatory drug (NSAID) selected from the group consisting of a salt of naproxen, diclofenac, ibuprofen, and combinations thereof; and a pharmaceutically acceptable anionic surfactant selected from the group consisting of sodium lauryl sulfate, docusate sodium, docusate calcium, and combinations thereof; wherein the opioid (including salts thereof), the salt of an NSAID, and the anionic surfactant are within the hydrophilic matrix. Preferred such compositions have a release profile comprising a substantial portion that is representative of zero-order release kinetics under in vitro conditions.

In preferred compositions, the opioid is an opioid that has analgesic activity (i.e., an opioid analgesic). Thus, compositions of the present invention are preferably used in methods of preventing, alleviating, or ameliorating the level of pain in a subject. Alternatively, compositions of the present invention can be used in suppressing a cough.

In a preferred embodiment, the present invention provides a sustained-release oral pharmaceutical composition comprising within a single dosage form: a hydrophilic matrix; a therapeutically effective amount of an opioid selected from the group consisting of hydrocodone, tramadol, salts thereof, and combinations thereof; and a salt of a non-steroidal anti-inflammatory drug (NSAID) selected from the group consisting of a salt of naproxen, diclofenac, ibuprofen, and combinations thereof; wherein the opioid (including salts thereof) and the salt of an NSAID are within the hydrophilic matrix; wherein the composition exhibits a release profile comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an opioid selected from the group consisting of hydrocodone, a salt thereof, and combinations thereof; and a salt of a non-steroidal anti-inflammatory drug (NSAID) selected from the group consisting of a salt of naproxen, and combinations thereof; wherein the opioid (including salts thereof) and the salt of an NSAID are within the hydrophilic matrix; wherein the composition exhibits a release profile comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an opioid selected from the group consisting of tramadol, a salt thereof, and combinations thereof; and a salt of a non-steroidal anti-inflammatory drug (NSAID) selected from the group consisting of a salt of naproxen, and combinations thereof; wherein the opioid (including salts thereof) and the salt of an NSAID are within the hydrophilic matrix; wherein the composition exhibits a release profile comprising a substantial portion that is representative of zero-order release kinetics under in vitro conditions.

In a preferred embodiment, the present invention provides a sustained-release oral pharmaceutical composition comprising within a single dosage form: a hydrophilic matrix; a therapeutically effective amount of an opioid selected from the group consisting of hydrocodone, tramadol, salts thereof, and combinations thereof; a salt of a non-steroidal anti-inflammatory drug (NSAID) selected from the group consisting of a salt of naproxen, diclofenac, ibuprofen, and combinations thereof; and a pharmaceutically acceptable anionic surfactant selected from the group consisting of sodium lauryl sulfate, docusate sodium, docusate calcium, and combinations thereof; wherein the opioid (including salts thereof), the salt of an NSAID, and the anionic surfactant are within the hydrophilic matrix. Preferably, such composition exhibits a release profile comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an opioid selected from the group consisting of hydrocodone, a salt thereof, and combinations thereof; a salt of a non-steroidal anti-inflammatory drug (NSAID) selected from the group consisting of a salt of naproxen, and combinations thereof; and a pharmaceutically acceptable anionic surfactant selected from the group consisting of docusate sodium, docusate calcium, and combinations thereof; wherein the opioid (including salts thereof), the salt of an NSAID, and the anionic surfactant are within the hydrophilic matrix. Preferably, such composition exhibits a release profile comprising a substantial portion that is representative of zero-order release kinetics under in vitro conditions.

In a preferred embodiment, the present invention provides a sustained-release oral pharmaceutical composition comprising within a single dosage form: a hydrophilic matrix comprising a hydroxypropyl methylcellulose; a therapeutically effective amount of an opioid selected from the group consisting of tramadol, a salt thereof; and combinations thereof; a salt of a non-steroidal anti-inflammatory drug (NSAID) selected from the group consisting of a salt of naproxen, and combinations thereof; and a pharmaceutically acceptable anionic surfactant selected from the group consisting of docusate sodium, docusate calcium, and combinations thereof; wherein the opioid (including salts thereof), the salt of an NSAID, and the anionic surfactant are within the hydrophilic matrix. Preferably, such composition exhibits a release profile comprising a substantial portion that is representative of zero-order release kinetics under in vitro conditions.

In a preferred embodiment, the present invention provides a method of preventing, alleviating, or ameliorating the level of pain in a subject, the method administering to a subject a composition comprising: a hydrophilic matrix; a pain-reducing amount of an opioid analgesic (including salts thereof); and a salt of a non-steroidal anti-inflammatory drug (NSAID) present in an amount effective to provide zero-order release kinetics under in vitro conditions; wherein the opioid analgesic (including salts thereof) and salt of an NSAID are within the hydrophilic matrix; wherein the composition has a release profile comprising a substantial portion that is representative of zero-order release kinetics under in vitro conditions.

In a preferred embodiment, the present invention provides a method of preventing, alleviating, or ameliorating the level of pain in a subject, the method administering to a subject a composition comprising: a hydrophilic matrix; a therapeutically effective amount of an opioid analgesic (including salts thereof); a salt of a non-steroidal anti-inflammatory drug (NSAID); and a pharmaceutically acceptable anionic surfactant; wherein the opioid analgesic (including salts thereof), the salt of an NSAID, and the anionic surfactant are within the hydrophilic matrix. Preferably, such composition exhibits a release profile comprising a substantial portion that is representative of zero-order release kinetics under in vitro conditions.

In methods of the present invention, administering a composition of the present invention comprises administering once or twice per day, and often once per day.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a composition comprising "a" salt of a non-steroidal anti-inflammatory drug can be interpreted to mean that the composition includes "one or more" non-steroidal anti-inflammatory drugs. Similarly, a composition comprising "a" pharmaceutically acceptable anionic surfactant can be interpreted to mean that the composition includes "one or more" pharmaceutically acceptable anionic surfactants.

As used herein, the term "or" is generally employed in its sense including "and/or" unless the content clearly dictates otherwise. The term "and/or" means one or all of the listed elements or a combination of any two or more of the listed elements.

Also herein, all numbers are assumed to be modified by the term "about" and preferably by the term "exactly." Notwithstanding that the numerical ranges and parameters setting forth the broad scope of the invention are approximations, the numerical values set forth in the specific examples are reported as precisely as possible. All numerical values, however, inherently contain certain errors necessarily resulting from the standard deviation found in their respective testing measurements.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "up to" a particular value, that value is included within the range.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 1 and 2 show dissolution profiles in phosphate buffer for certain tramadol hydrochloride (TMD) formulations in accordance with embodiments of the present invention.

FIGS. 3 and 4 show dissolution profiles in phosphate buffer for certain Hydrocodone Bitartrate (HCB) formulations in accordance with embodiments of the present invention.

FIG. 5 shows dissolution profiles in acidic and hydroalcoholic media for certain dextromethorphan (DXM) formulations.

DETAILED DESCRIPTION OF ILLUSTRATIVE EMBODIMENTS

The present invention provides sustained-release oral pharmaceutical compositions and methods of use. Preferably, such compositions are used for pain treatment, cough suppression, or other indications typically requiring opioid administration. Such compositions are in a single dosage form and include an opioid (preferably an opioid analgesic) (including salts thereof), a salt of a non-steroidal anti-inflammatory drug (NSAID), and a hydrophilic matrix. Certain embodiments also include a pharmaceutically acceptable anionic surfactant.

Herein, sustained-release compositions release the opioid over a period of time greater than 60 minutes. Preferred sustained-release formulations demonstrate at least 60%, and more preferably at least 80%, release of the opioid over a desired period (e.g., a period of 8 to 12 hours). If desired, however, the formulations of the present invention could be tailored to release the opioid over any period from 6 hours to 24 hours or longer.

Particularly preferred sustained-release compositions of the present invention demonstrate a zero-order release profile with respect to the opioid under in vitro conditions, such as when tested in accordance with appropriate United States Pharmacopeia test methods. Herein, "zero-order" with respect to the opioid (including salts thereof) means a relatively constant rate of release (i.e., exhibiting a substantially linear release profile over a period of time, preferably at least a few hours). Although a small portion (e.g., the initial 30-60 minutes) of the release profile may not be zero-order (e.g., as in a formulation containing an immediate-release coating, or a bilayer or multi-layer formulation comprising an immediate-release layer), a substantial portion (e.g., several hours), and preferably a major portion, of the release profile is representative of zero-order release kinetics.

Opioids and Salts Thereof

An opioid is a chemical substance that works by binding to opioid receptors, which are found principally in the central nervous system and the gastrointestinal tract. The receptors in these two organ systems mediate both the beneficial effects, and the undesirable side effects. There are three principal classes of opioid receptors, $\mu$, $\kappa$, $\delta$ (mu, kappa, and delta), although up to seventeen have been reported, and include the $\epsilon$, $\iota$, $\lambda$, and $\zeta$ (Epsilon, Iota, Lambda and Zeta) receptors. There are three subtypes of $\mu$ receptor: $\mu_1$ and $\mu_2$, and the newly discovered $\mu_3$. Another receptor of clinical importance is the opioid-receptor-like receptor 1 (ORL1), which is involved in pain responses as well as having a major role in the development of tolerance to $\mu$-opioid agonists used as analgesics. An opioid can have agonist characteristics, antagonist characteristics, or both (e.g., pentazocine is a synthetic mixed agonist-antagonist opioid analgesic of the benzomorphan class of opioids used to treat mild to moderately severe pain). The main use for opioids is for pain relief, although cough suppression is also a common use. For example, hydromorphone is used to relieve moderate to severe pain and severe, painful dry coughing. Hydrocodone is most commonly used as an intermediate-strength analgesic and strong cough suppressant.

There are a number of broad classes of opioids: natural opiates, which are alkaloids contained in the resin of the opium poppy, and include morphine and codeine; semi-synthetic opiates, created from the natural opioids, such as hydromorphone (found in Dilaudid), hydrocodone (found in Vicodin), oxycodone (found in Oxycontin and Percocet), oxymorphone, desomorphine, diacetylmorphine (Heroin), nicomorphine, buprenorphine, dihydrocodeine, and benzylmorphine; and fully synthetic opioids, such as fentanyl, methadone, tramadol, and propoxyphene (found in Darvon and Darvocet N). Other examples of opioids include levorphanol, meperidine (found in Demerol), pentazocine, tilidine, and others disclosed, for example, at www.opioids.com.

Certain opioids have antagonist action. For example, naloxone is a $\mu$-opioid receptor competitive antagonist. Naloxone is a drug used to counter the effects of opioid overdose, for example heroin or morphine overdose. Naltrexone is an opioid receptor antagonist used primarily in the management of alcohol dependence and opioid dependence. N-methyl naltrexone is also an opioid receptor antagonist.

Various combinations of such compounds can be used if desired. Each of these compounds includes a tertiary amine as shown, wherein the amine nitrogen may or may not be within a ring:
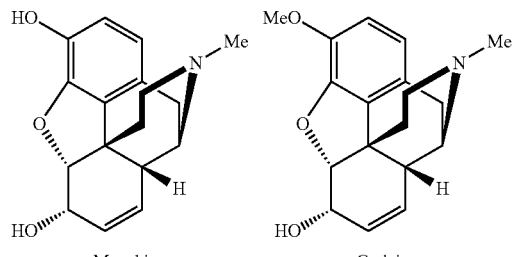
Morphine    Codeine
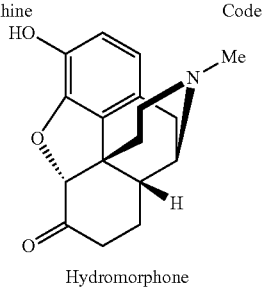
Hydromorphone
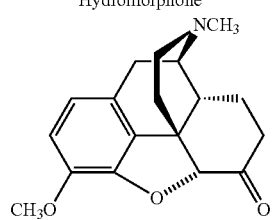
Hydrocodone
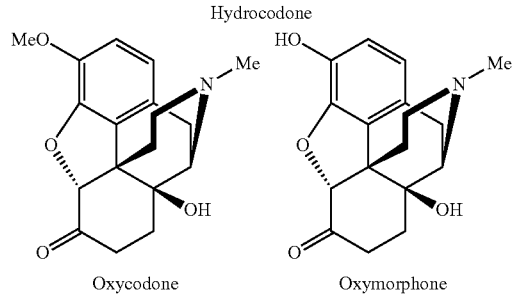
Oxycodone    Oxymorphone
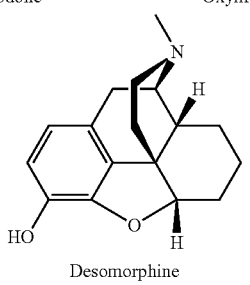
Desomorphine
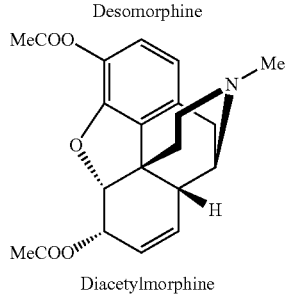
Diacetylmorphine
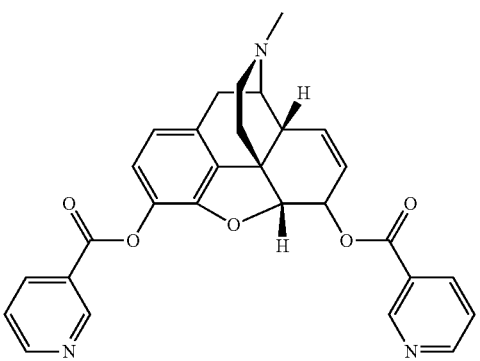
Nicomorphine
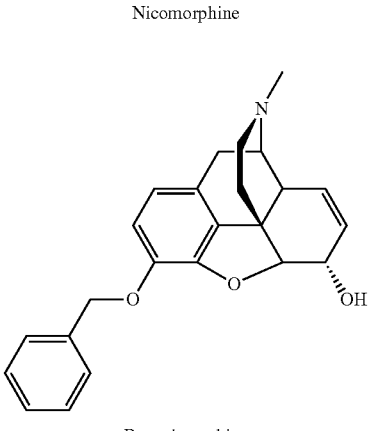
Benzylmorphine
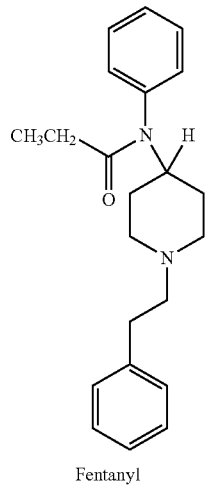
Fentanyl
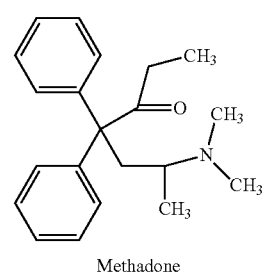
Methadone

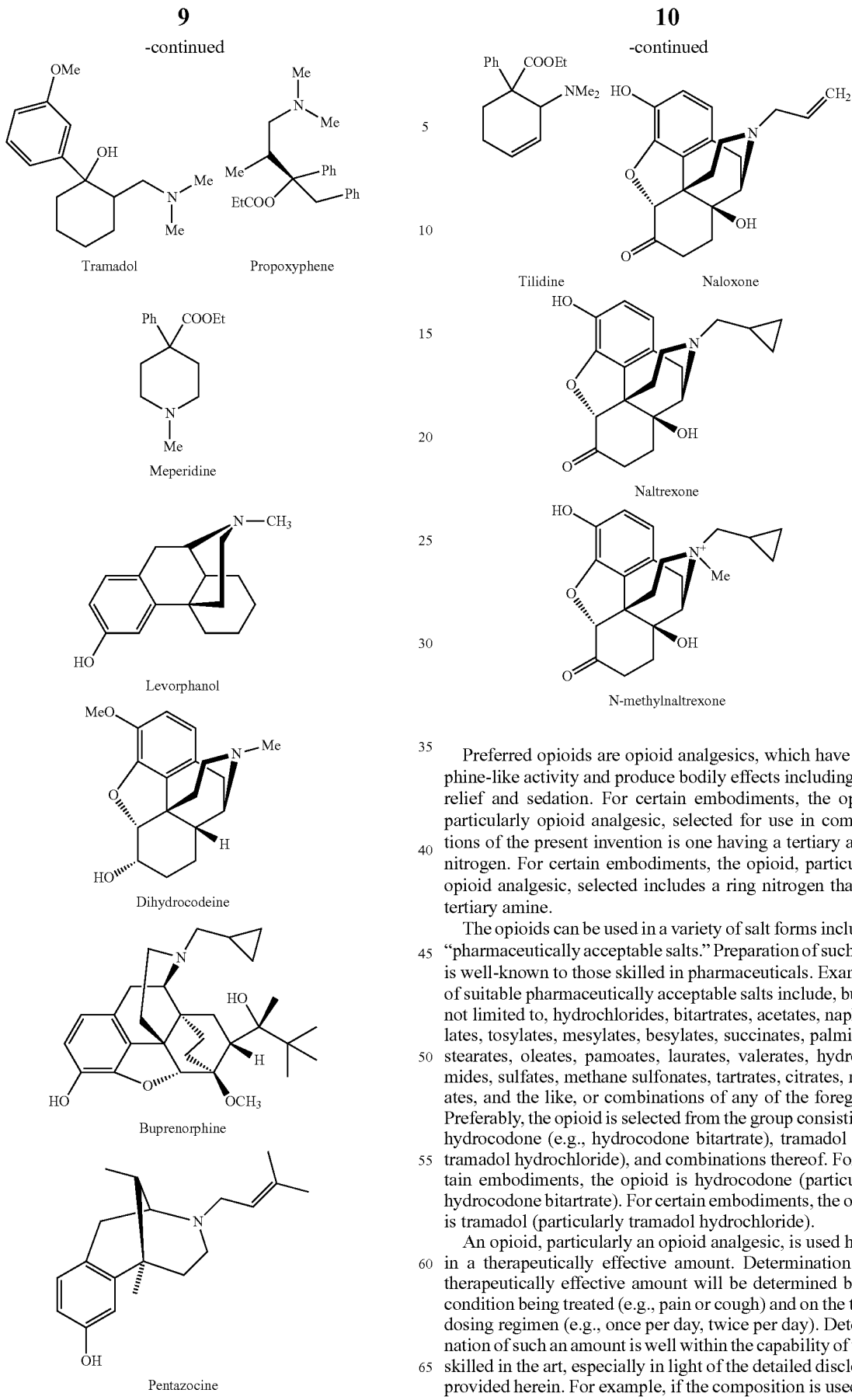

Preferred opioids are opioid analgesics, which have morphine-like activity and produce bodily effects including pain relief and sedation. For certain embodiments, the opioid, particularly opioid analgesic, selected for use in compositions of the present invention is one having a tertiary amine nitrogen. For certain embodiments, the opioid, particularly opioid analgesic, selected includes a ring nitrogen that is a tertiary amine.

The opioids can be used in a variety of salt forms including "pharmaceutically acceptable salts." Preparation of such salts is well-known to those skilled in pharmaceuticals. Examples of suitable pharmaceutically acceptable salts include, but are not limited to, hydrochlorides, bitartrates, acetates, naphthylates, tosylates, mesylates, besylates, succinates, palmitates, stearates, oleates, pamoates, laurates, valerates, hydrobromides, sulfates, methane sulfonates, tartrates, citrates, maleates, and the like, or combinations of any of the foregoing. Preferably, the opioid is selected from the group consisting of hydrocodone (e.g., hydrocodone bitartrate), tramadol (e.g., tramadol hydrochloride), and combinations thereof. For certain embodiments, the opioid is hydrocodone (particularly hydrocodone bitartrate). For certain embodiments, the opioid is tramadol (particularly tramadol hydrochloride).

An opioid, particularly an opioid analgesic, is used herein in a therapeutically effective amount. Determination of a therapeutically effective amount will be determined by the condition being treated (e.g., pain or cough) and on the target dosing regimen (e.g., once per day, twice per day). Determination of such an amount is well within the capability of those skilled in the art, especially in light of the detailed disclosure provided herein. For example, if the composition is used as a cough suppressant, the amount of the opioid would be that which is effective for suppressing a cough. If the composition is used to treat pain, a therapeutically effective amount or an opioid is referred to herein as a "pain-reducing amount." Herein, this means an amount of compound effective to reduce or treat (i.e., prevent, alleviate, or ameliorate) pain symptoms over the desired time period. This amount can vary with each specific opioid depending on the potency of each. For example, for hydrocodone, the amount per single dosage form of the present invention may be 5 mg to 50 mg.

Salts of Non-Steroidal Anti-Inflammatory Drugs (NSAIDs)

Compositions of the present invention include one or more non-steroidal anti-inflammatory drugs, usually abbreviated to NSAIDs or NAIDs. These are drugs with analgesic, antipyretic and, in higher doses, anti-inflammatory effects.

NSAIDs are sometimes also referred to as non-steroidal anti-inflammatory agents/analgesics (NSAIAs) or non-steroidal anti-inflammatory medicines (NSAIMs). All NSAIDs as used herein are nonspecific COX inhibitors.

Surprisingly, in the practice of the present invention, salts of NSAIDs (but not the free bases) provide compositions with zero-order release kinetics with respect to the opioids (including salts thereof).

There are roughly seven major classes of NSAIDs, including:

(1) salicylate derivatives, such as acetylsalicylic acid (aspirin), amoxiprin, benorylate/benorilate, choline magnesium salicylate, diflunisal, ethenzamide, faislamine, methyl salicylate, magnesium salicylate, salicyl salicylate, and salicylamide; a few structures of such compounds are as follows:

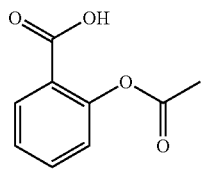
Acetylsalicylic acid (aspirin)

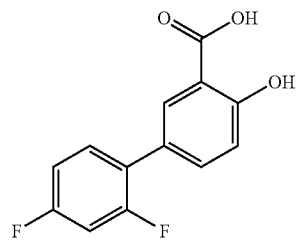
Diflunisal

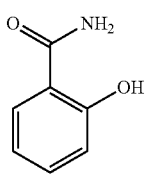
Salicylamide (2) 2-aryl propionic acid derivatives, such as ibuprofen, ketoprofen, alminoprofen, carprofen, dexibuprofen, dexketoprofen, fenbufen, fenoprofen, flunoxaprofen, flurbiprofen, ibuproxam, ondoprofen, ketorolac, loxoprofen, naproxen, oxaprozin, pirprofen, suprofen, and tiaprofenic acid; a few structures of such compounds are as follows:

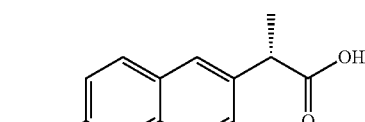
Naproxen

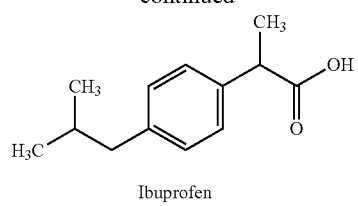
Ibuprofen

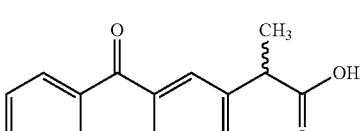
Ketoprofen

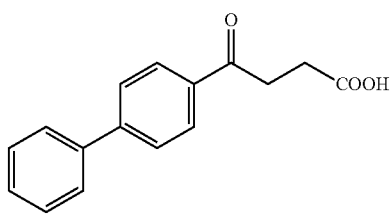
Fenbufen (3) pyrazolidine derivatives, such as phenylbutazone, ampyrone, azapropazone, clofezone, kebuzone, metamizole, mofebutazone, oxyphenbutazone, phenazone, and sulfinpyrazone; a few structures of such compounds are as follows:

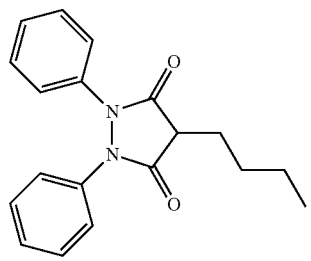
Phenylbutazone

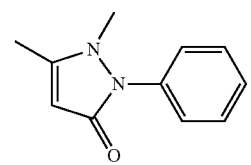
Phenazone

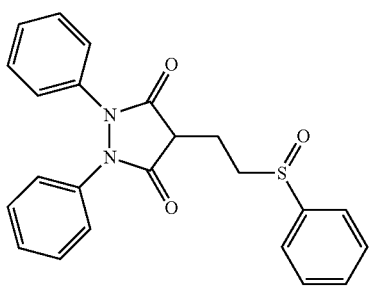
Sulfinpyrazone (4) N-arylanthranilic acid (or fenamate) derivatives, such as mefenamic acid, flufenamic acid, meclofenamic acid, tolfenamic acid, and esters thereof; a few structures of such compounds are as follows:

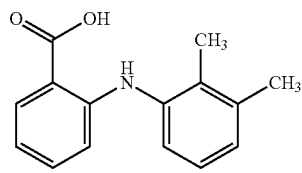

Mefenamic acid

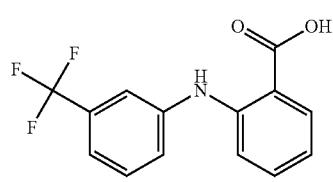

Flufenamic acid

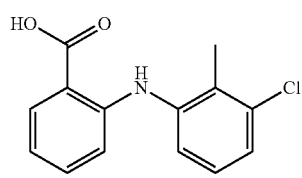

Tolfenamic acid (5) oxicam derivatives, such as piroxicam, droxicam, lornoxicam, meloxicam, and tenoxicam; a few structures of such compounds are as follows:

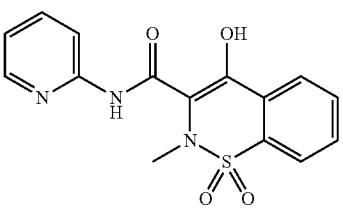

Piroxicam

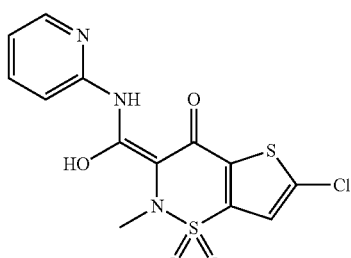

Lornoxicam

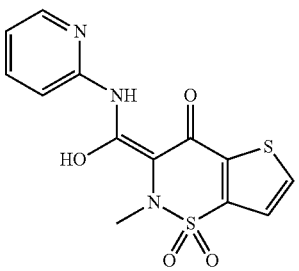

Tenoxicam (6) arylalkanoic acids, such as diclofenac, aceclofenac, acemethacin, alclofenac, bromfenac, etodolac, indomethacin, nabumetone, oxametacin, proglumetacin, sulindac (prodrug), and tolmetin; a few structures of such compounds are as follows:

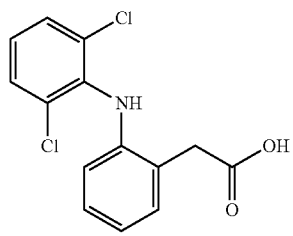

Diclofenac

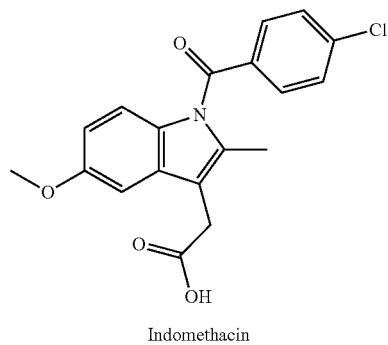 [SMILES: COc1ccc2c(c1)c(CC(=O)O)c(C)n2C(=O)c1ccc(Cl)cc1]

Indomethacin

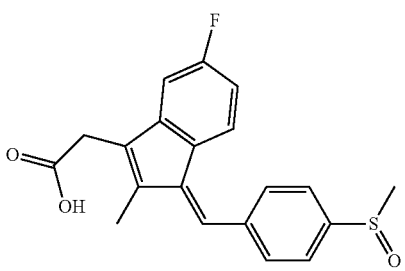

Sulindac (7) indole derivatives, such as indomethacin, the structure of which is as follows:

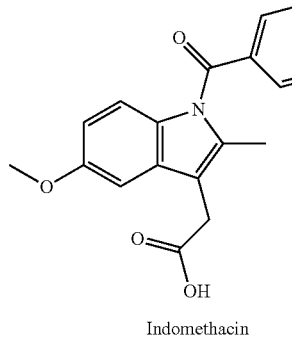

Indomethacin

Although acetaminophen (paracetamol) is an analgesic and it is sometimes grouped with NSAIDs, it is not an NSAID (particularly for the purposes of the present invention) because it does not have any significant anti-inflammatory activity.

NSAIDs used in compositions of the present invention are pharmaceutically acceptable salts thereof. Typically, such salts include metal salts, such as sodium, calcium, or potassium salts. Salts such as bismuth salts, magnesium salts, or zinc salts may also be suitable. Various combinations of counterions and/or NSAID salts can be used if desired.

Preferred NSAID salts include a terminal carboxylic acid or terminal carboxylate group on the active moiety. In certain embodiments, the NSAID salts include a terminal carboxylic acid group on the active moiety. In certain embodiments, the NSAID salts include a terminal carboxylate group on the active moiety. Exemplary such NSAID salts are selected from the group consisting of a salicylate derivative, a 2-aryl propionic acid derivative, an N-arylanthranilic acid derivative, an aryl alkanoic acid, an indole derivative, and combinations thereof. Preferred NSAID salts include salts of 2-aryl propionic acid derivative (e.g., naproxen and ibuprofen), aryl alkanoic acids, or combinations thereof. Particularly preferred NSAID salts include naproxen sodium, ibuprofen sodium, diclofenac sodium, and combinations thereof. Structures of naproxen, diclofenac, and ibuprofen are as follows:

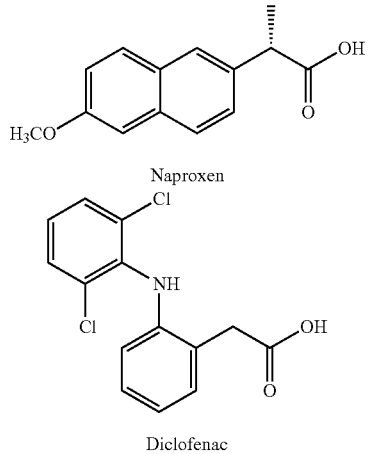

Naproxen

Diclofenac

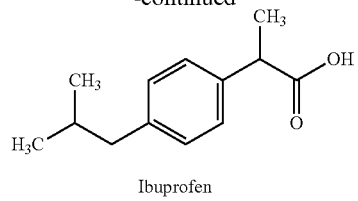

Ibuprofen

In preferred compositions, an NSAID salt is present in compositions of the present invention in an amount to provide zero-order release kinetics under in vitro conditions. Such amount can be a sub-therapeutic amount or it can be a conventional therapeutic amount. Determination of such an amount is well within the capability of those skilled in the art, especially in light of the detailed disclosure provided herein. For example, naproxen sodium could be included in a single dosage form of the current invention at an amount of 220 mg to 750 mg (for a twice per day dosage form).

Pharmaceutically Acceptable Anionic Surfactants

Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfur-containing surfactants (e.g., sulfuric acid esters, alkyl sulfates such as sodium lauryl sulfate (SLS), ethoxylated alkyl sulfates, ester linked sulfonates such as docusate sodium or dioctyl sodium succinate (DSS), and alpha olefin sulfonates), and phosphated ethoxylated alcohols. Preferred surfactants are on the GRAS ("Generally Recognized as Safe") list. Various combinations of pharmaceutically acceptable anionic surfactants can be used if desired.

In certain embodiments, the pharmaceutically acceptable anionic surfactant is a sulfur-containing surfactant, and particularly an alkyl sulfate, an ester-linked sulfonate, and combinations thereof. Preferred pharmaceutically acceptable anionic surfactants include sodium lauryl sulfate, docusate (i.e., dioctyl sulfosuccinate) sodium, docusate calcium, and combinations thereof. A particularly preferred anionic surfactant is docusate sodium. The structures of docusate sodium and sodium lauryl sulfate are as follows:

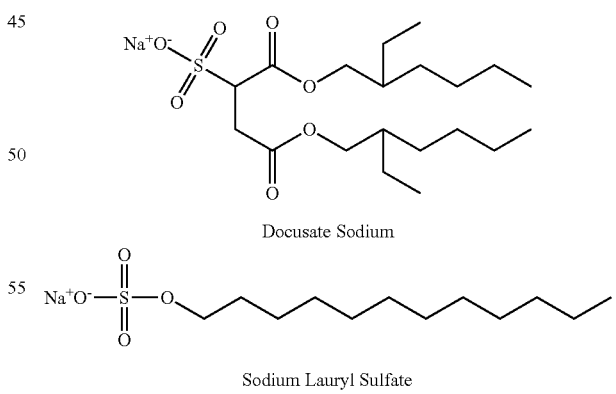

Docusate Sodium

Sodium Lauryl Sulfate

In preferred embodiments, a pharmaceutically acceptable anionic surfactant is present in compositions of the present invention in a release-modifying amount. A wide range of amounts can be used to tailor the rate and extent of release. Determination of such an amount is well within the capability of those skilled in the art, especially in light of the detailed disclosure provided herein.

In some embodiments, certain surfactants such as docusate can function as a stool softener when used at a therapeutic level; however, sub-therapeutic amounts can be used for release modification.

Such surfactants can be used for their abuse deterrence effects. For example, a surfactant could function as a nasal irritant, which would make crushing and inhaling the compositions undesirable. Also, a mixture of an opioid and a surfactant (e.g., docusate) in a hydrophilic matrix is difficult to extract and separate into the individual components, and injection of the mixture is undesirable and/or unsafe.

Hydrophilic Matrix and Other Excipients

Compositions of the present invention include a hydrophilic matrix, wherein the opioid (including salts thereof), the salt of an NSAID, and the optional anionic surfactant are within (e.g., mixed within) the hydrophilic matrix. Such matrix preferably includes at least one hydrophilic polymeric compound. The hydrophilic polymeric compound preferably forms a matrix that releases the opioid, preferably opioid analgesic, or the pharmaceutically acceptable salt thereof at a sustained rate upon exposure to liquids. The rate of release of the opioid or the pharmaceutically acceptable salt thereof from the hydrophilic matrix typically depends, at least in part, on the opioid's partition coefficient between the components of the hydrophilic matrix and the aqueous phase within the gastrointestinal tract.

The sustained-release composition generally includes at least one hydrophilic polymeric compound in an amount of 10% to 90% by weight, preferably in an amount of 20% to 80% by weight, based on the total weight of the composition.

The hydrophilic polymeric compound may be any known in the art. Exemplary hydrophilic polymeric compounds include gums, cellulose ethers, acrylic resins, polyvinyl pyrrolidone, protein-derived compounds, and combinations thereof. Exemplary gums include heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include hydroxyalkyl celluloses and carboxyalkyl celluloses. Preferred cellulose ethers include hydroxyethyl celluloses, hydroxypropyl celluloses, hydroxypropyl methylcelluloses, carboxy methylcelluloses, and mixtures thereof. Exemplary acrylic resins include polymers and copolymers of acrylic acid, methacrylic acid, methyl acrylate, and methyl methacrylate. Various combinations of hydrophilic compounds can be used for various effects.

In some embodiments, the hydrophilic compound is preferably a cellulose ether. Exemplary cellulose ethers include those commercially available under the trade designation METHOCEL Premium from Dow Chemical Co. Such methylcellulose and hypromellose (i.e., hydroxypropyl methylcellulose) products are a broad range of water-soluble cellulose ethers that enable pharmaceutical developers to create formulas for tablet coatings, granulation, sustained release, extrusion, and molding. For certain embodiments, the cellulose ether comprises a hydroxypropyl methylcellulose.

Varying the types of cellulose ethers can impact the release rate. For example, varying the types of METHOCEL cellulose ethers, which have different viscosities of 2% solutions in water (METHOCEL K4M Premium hypromellose 2208 (19-24% methoxy content; 7-12% hydroxypropyl content; 3,000-5,600 cps of a 2% solution in water); METHOCEL K15M Premium hypromellose 2208 (19-24% methoxy content; 7-12% hydroxypropyl content; 11,250-21,000 cps of a 2% solution in water); and METHOCEL K100M Premium hypromellose 2208 (19-24% methoxy content; 7-12% hydroxypropyl content; 80,000-120,000 cps of a 2% solution in water)) can help tailor release rates.

Compositions of the present invention can also include one or more excipients such as lubricants, glidants, flavorants, coloring agents, stabilizers, binders, fillers, disintegrants, diluents, suspending agents, viscosity enhancers, wetting agents, buffering agents, control release agents, crosslinking agents, preservatives, and the like. Such compounds are well known in the art of drug release and can be used in various combinations.

One particularly useful excipient that can form at least a portion of a composition of the present invention is a binder that includes, for example, a cellulose such as microcrystalline cellulose. An exemplary microcrystalline cellulose is that available under the trade designation AVICEL PH (e.g., AVICEL PH-101, AVICEL PH-102, AVICEL PH-301, AVICEL PH-302, and AVICEL RC-591) from FMC BioPolymers. The sustained-release composition generally includes at least one microcrystalline cellulose in an amount of 3 wt-% to 50 wt-%, based on the total weight of the composition.

Other additives can be incorporated into compositions of the present invention to further modify the rate and extent of release. For example, a non-pharmacologically active amine, such as tromethamine, triethanolamine, betaine, benzathine, or erbumine could be included in the compositions of the present invention to further modify the release rate.

Compositions of the present invention can optionally include compounds that function as abuse deterrents. For example, opioid antagonists (e.g., naltrexone, N-methylnaltrexone, naloxone) can be combined with opioid agonists to deter parenteral abuse of opioid agonists. Such opioid agonist/antagonist combinations can be chosen such that the opioid agonist and opioid antagonist are only extractable from the dosage form together, and at least a two-step extraction process is required to separate the opioid antagonist from the opioid agonist. The amount of opioid antagonist is sufficient to counteract opioid effects if extracted together and administered parenterally and/or the amount of antagonist is sufficient to cause the opioid agonist/antagonist combination to provide an aversive effect in a physically dependent human subject when the dosage form is orally administered. Typically, such compositions are formulated in such a way that if the dosage form is not tampered with, the antagonist passes through the GI tract intact; however, upon crushing, chewing, dissolving, etc., the euphoria-curbing antagonist is released.

In a similar fashion, compounds that cause nausea could be added to the formulation to prevent abusers from taking more than the intended dose. These components are added to the formulation at sub-therapeutic levels, such that no adverse effects are realized when the correct dose is taken.

Also, compositions of the present invention can include an aversive agent such as a dye (e.g., one that stains the mucous membrane of the nose and/or mouth) that is released when the dosage form is tampered with and provides a noticeable color or dye which makes the act of abuse visible to the abuser and to others such that the abuser is less likely to inhale, inject, and/or swallow the tampered dosage form. Examples of various dyes that can be employed as the aversive agent, including for example, and without limitation, FD&C Red No. 3, FD&C Red No. 20, FD&C Yellow No. 6, FD&C Blue No. 1, FD&C Blue No. 2, FD&C Green No. 1, FD&C Green No. 3, FD&C Green No. 5, FD&C Red No. 30, D&C Orange No. 5, D&C Red No. 8, D&C Red No. 33, caramel, and ferric oxide, red, other FD&C dyes and lakes, and natural coloring agents such as grape skin extract, beet red powder, beta-carotene, annato, carmine, turmeric, paprika, and combinations thereof.

The sustained-release compositions of the present invention may also include one or more hydrophobic polymers. The hydrophobic polymers may be used in an amount sufficient to slow the hydration of the hydrophilic compound without disrupting it. For example, the hydrophobic polymer may be present in an amount of 0.5% to 20% by weight, based on the total weight of the composition.

Exemplary hydrophobic polymers include alkyl celluloses (e.g., $C_{1-6}$ alkyl celluloses, carboxymethylcellulose, ethylcellulose), other hydrophobic cellulosic materials or compounds (e.g., cellulose acetate phthalate, hydroxypropylmethylcellulose phthalate), polyvinyl acetate polymers (e.g., polyvinyl acetate phthalate), polymers or copolymers derived from acrylic and/or methacrylic acid esters, zein, waxes (e.g., carnauba wax), shellac, hydrogenated vegetable oils, and combinations thereof.

Pharmaceutical Compositions

Pharmaceutical compositions of the present invention are single dosage forms that can be in a form capable of providing sustained release of the opioid. Herein, a "single dosage form" refers to the components of the composition be included within one physical unit (e.g., one tablet), whether it be in a uniform matrix, a multilayered construction, or some other configuration. Most commonly, this includes a tablet, which can include molded tablets, compressed tablets, or freeze-dried tablets. Other possible solid forms include pills, pellets, particulate forms (e.g., beads, powders, granules), and capsules (e.g., with particulate therein).

A single dosage form can be a coated dosage form with, for example, an outer layer of an immediate-release (IR) material (e.g., an opioid, an NSAID, or both, a release-modifying agent, a film coating for taste masking or for ease of swallowing, or the like), with a sustained-release (SR) core. Typically, such coated formulations do not demonstrate zero-order release kinetics during the initial immediate-release phase, but preferably demonstrate zero-order release kinetics during the dissolution of the sustained-release core.

A single dosage form can be incorporated into a multilayered dosage form (e.g., tablet). For example, a bilayer tablet could be formulated to include a layer of a conventional immediate-release matrix and a layer of a sustained-release composition of the present invention. Optionally, a multilayered dosage form could be coated.

Pharmaceutical compositions for use in accordance with the present invention may be formulated in a conventional manner to incorporate one or more physiologically acceptable carriers comprising excipients and auxiliaries. Compositions of the invention may be formulated as tablets, pills, capsules, and the like, for oral ingestion by a patient to be treated.

Pharmaceutical compositions of the present invention may be manufactured in a manner that is itself known, e.g., by means of conventional mixing, granulating, encapsulating, entrapping, or tabletting processes.

Pharmaceutical compositions suitable for use in the present invention include compositions where the ingredients are contained in an amount effective to achieve its intended purpose. The exact formulation, route of administration, and dosage for the pharmaceutical compositions of the present invention can be chosen by the individual physician in view of the patient's condition. (See, e.g., Fingl et al. in "The Pharmacological Basis of Therapeutics", Ch. 1, p. 1 (1975)). The exact dosage will be determined on a drug-by-drug basis, in most cases. Dosage amount and interval may be adjusted individually to provide plasma levels of the active ingredients/moieties that are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. The amount of composition administered will, of course, be dependent on the subject being treated, on the subject's weight, the severity of the pain, the manner of administration, and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert.

It will be understood by those of skill in the art that numerous and various modifications can be made without departing from the spirit of the present invention. Therefore, it should be clearly understood that the forms of the present invention are illustrative only and are not intended to limit the scope of the present invention.

Exemplary Embodiments of the Invention

1. A sustained-release oral pharmaceutical composition comprising within a single dosage form:
   a hydrophilic matrix;
   a therapeutically effective amount of an opioid (including salts thereof); and
   a salt of a non-steroidal anti-inflammatory drug (NSAID);
   wherein the opioid and the salt of an NSAID are within the hydrophilic matrix; and
   wherein the composition exhibits a release profile comprising a substantial portion that is representative of zero-order release kinetics under in vitro conditions.

2. A sustained-release oral pharmaceutical composition comprising within a single dosage form:
   a hydrophilic matrix;
   a therapeutically effective amount of an opioid (including salts thereof);
   a salt of a non-steroidal anti-inflammatory drug (NSAID); and
   a pharmaceutically acceptable anionic surfactant;
   wherein the opioid, the salt of an NSAID, and the anionic surfactant are within the hydrophilic matrix.

3. The composition of embodiment 2 which exhibits a release profile comprising a substantial portion that is representative of zero-order release kinetics under in vitro conditions.

4. The composition of any one of embodiments 1 through 3 wherein the opioid has analgesic properties.

5. The composition of any one of embodiments 1 through 4 wherein the opioid comprises a tertiary amine.

6. The composition of embodiment 5 wherein the opioid comprises a ring nitrogen that is a tertiary amine.

7. The composition of any one of embodiments 1 through 6 wherein the opioid is selected from the group consisting of morphine, codeine, hydromorphone, hydrocodone, oxycodone, oxymorphone, desomorphine, diacetylmorphine, buprenorphine, dihydrocodeine, nicomorphine, benzylmorphine, fentanyl, methadone, tramadol, propoxyphene, levorphanol, meperidine, and combinations thereof.

8. The composition of any one of embodiments 1 through 7 wherein the opioid is a salt comprising a hydrochloride, a bitartrate, an acetate, a naphthylate, a tosylate, a mesylate, a besylate, a succinate, a palmitate, a stearate, an oleate, a pamoate, a laurate, a valerate, a hydrobromide, a sulfate, a methane sulfonate, a tartrate, a citrate, a maleate, or a combination of the foregoing.

9. The composition of embodiment 7 or embodiment 8 wherein the opioid is selected from the group consisting of hydrocodone, tramadol, salts thereof, and combinations thereof.

10. The composition of embodiment 9 wherein the opioid is selected from the group consisting of hydrocodone bitartrate, tramadol hydrochloride, and combinations thereof 11. The composition of any one of embodiments 7 through 9 wherein the opioid is selected from the group consisting of hydrocodone, a salt thereof, and combinations thereof 12. The composition of embodiment 11 wherein the opioid comprises hydrocodone bitartrate.

13. The composition of any one of embodiments 7 through 9 wherein the opioid is selected from the group consisting of tramadol, a salt thereof, and combinations thereof.

14. The composition of embodiment 13 wherein the opioid comprises tramadol hydrochloride.

15. The composition of any one of the preceding embodiments wherein the NSAID salt is selected from the group consisting of a salicylate derivative, a 2-aryl propionic acid derivative, a pyrazolidine derivative, an N-arylanthranilic acid derivative, an oxicam derivative, an arylalkanoic acid, an indole derivative, and combinations thereof 16. The composition of embodiment 15 wherein the NSAID salt comprises a terminal carboxylic acid group or terminal carboxylate group.

17. The composition of embodiment 16 wherein the NSAID salt is selected from the group consisting of a salicylate derivative, a 2-aryl propionic acid derivative, an N-arylanthranilic acid derivative, an aryl alkanoic acid, an indole derivative, and combinations thereof 18. The composition of embodiment 17 wherein the NSAID salt is a 2-aryl propionic acid derivative, an aryl alkanoic acid, or combinations thereof 19. The composition of embodiment 18 wherein the NSAID salt is selected from the group consisting of a salt of naproxen, diclofenac, ibuprofen, and combinations thereof.

20. The composition of embodiment 19 wherein the NSAID salt is selected from the group consisting of naproxen sodium, diclofenac sodium, ibuprofen sodium, and combinations thereof.

21. The composition of any one of embodiments 2 through 20, as they depend on embodiment 2, wherein the pharmaceutically acceptable anionic surfactant is selected from the group consisting of monovalent alkyl carboxylates, acyl lactylates, alkyl ether carboxylates, N-acyl sarcosinates, polyvalent alkyl carbonates, N-acyl glutamates, fatty acid-polypeptide condensates, sulfur-containing surfactants, phosphated ethoxylated alcohols, and combinations thereof.

22. The composition of embodiment 21 wherein the pharmaceutically acceptable anionic surfactant is a sulfur-containing surfactant.

23. The composition of embodiment 22 wherein the sulfur-containing surfactant is selected from the group consisting of an alkyl sulfate, an ester-linked sulfonate, and combinations thereof.

24. The composition of embodiment 23 wherein the pharmaceutically acceptable anionic surfactant is selected from the group consisting of sodium lauryl sulfate, docusate sodium, docusate calcium, and combinations thereof.

25. The composition of embodiment 24 wherein the pharmaceutically acceptable anionic surfactant is docusate sodium.

26. The composition of any one of the preceding embodiments wherein the opioid is present in a pain-reducing amount.

27. The composition of any one of the preceding embodiments wherein the NSAID salt is present in an amount effective to provide zero-order release kinetics under in vitro conditions.

28. The composition of any one of the preceding embodiments wherein the pharmaceutically acceptable anionic surfactant is present in a release-modifying amount.

29. The composition of any one of the preceding embodiments wherein the single dosage form is a tablet form.

30. The composition of embodiment 29 wherein the single dosage form tablet comprises a unitary matrix.

31. The composition of embodiment 29 wherein the single dosage form tablet comprises a multilayer tablet.

32. The composition of embodiment 31 wherein the single dosage form comprises an outer layer of an immediate-release (IR) material and a sustained-release (SR) core.

33. The composition of embodiment 32 wherein the IR material comprises an opioid, an NSAID, or both.

34. The composition of any one of the previous embodiments wherein the hydrophilic matrix comprises at least one hydrophilic polymeric compound selected from the group consisting of a gum, a cellulose ether, an acrylic resin, a polyvinyl pyrrolidone, a protein-derived compound, and combinations thereof.

35. The composition of embodiment 34 wherein the hydrophilic polymeric compound comprises a cellulose ether.

36. The composition of embodiment 35 wherein the cellulose ether comprises a hydroxyalkyl cellulose, a carboxyalkyl cellulose, and combinations thereof.

37. The composition of embodiment 35 wherein the cellulose ether comprises a methylcellulose, a hydroxypropyl methylcellulose, and combinations thereof.

38. The composition of embodiment 37 wherein the cellulose ether comprises a hydroxypropyl methylcellulose.

39. The composition of any one of the previous embodiments further including one or more excipients.

40. The composition of embodiment 39 wherein the excipients comprise lubricants, glidants, flavorants, coloring agents, stabilizers, binders, fillers, disintegrants, diluents, suspending agents, viscosity enhancers, wetting agents, buffering agents, control release agents, crosslinking agents, preservatives, and combinations thereof.

41. The composition of embodiment 40 comprising a binder.

42. The composition of embodiment 41 wherein the binder comprises a microcrystalline cellulose.

43. A sustained-release oral pharmaceutical composition comprising within a single dosage form:
a hydrophilic matrix;
a therapeutically effective amount of an opioid selected from the group consisting of hydrocodone, tramadol, salts thereof, and combinations thereof; and a salt of a non-steroidal anti-inflammatory drug (NSAID) selected from the group consisting of a salt of naproxen, diclofenac, ibuprofen, and combinations thereof;
wherein the opioid and the salt of an NSAID are within the hydrophilic matrix; and
wherein the composition exhibits a release profile comprising a substantial portion that is representative of zero-order release kinetics under in vitro conditions.

44. The composition of embodiment 43 wherein the opioid is selected from the group consisting of hydrocodone, a salt thereof, and combinations thereof.

45. The composition of embodiment 44 wherein the opioid comprises hydrocodone bitartrate.

46. The composition of embodiment 43 wherein the opioid is selected from the group consisting of tramadol, a salt thereof, and combinations thereof.

47. The composition of embodiment 46 wherein the opioid comprises tramadol hydrochloride.

48. The composition of any one of embodiments 43 through 47 wherein the NSAID salt is selected from the group consisting of naproxen sodium, diclofenac sodium, ibuprofen sodium, and combinations thereof.

49. The composition of any one of embodiments 43 through 48 wherein the hydrophilic polymeric compound comprises a cellulose ether.

50. The composition of embodiment 49 wherein the cellulose ether comprises a hydroxyalkyl cellulose, a carboxyalkyl cellulose, and combinations thereof.

51. The composition of embodiment 50 wherein the cellulose ether comprises a methylcellulose, a hydroxypropyl methylcellulose, and combinations thereof.

52. The composition of embodiment 51 wherein the cellulose ether comprises a hydroxypropyl methylcellulose.

53. A sustained-release oral pharmaceutical composition comprising within a single dosage form:
a hydrophilic matrix comprising a hydroxypropyl methylcellulose;
a therapeutically effective amount of an opioid selected from the group consisting of hydrocodone, a salt thereof, and combinations thereof; and
a salt of a non-steroidal anti-inflammatory drug (NSAID) selected from the group consisting of a salt of naproxen, and combinations thereof;
wherein the opioid and the salt of an NSAID are within the hydrophilic matrix; and
wherein the composition exhibits a release profile comprising a substantial portion that is representative of zero-order release kinetics under in vitro conditions.

54. A sustained-release oral pharmaceutical composition comprising within a single dosage form:
a hydrophilic matrix comprising a hydroxypropyl methylcellulose;
a therapeutically effective amount of an opioid selected from the group consisting of tramadol, a salt thereof, and combinations thereof; and
a salt of a non-steroidal anti-inflammatory drug (NSAID) selected from the group consisting of a salt of naproxen, and combinations thereof;
wherein the opioid and the salt of an NSAID are within the hydrophilic matrix; and
wherein the composition exhibits a release profile comprising a substantial portion that is representative of zero-order release kinetics under in vitro conditions.

55. A sustained-release oral pharmaceutical composition comprising within a single dosage form:
a hydrophilic matrix;
a therapeutically effective amount of an opioid selected from the group consisting of hydrocodone, tramadol, salts thereof; and combinations thereof;
a salt of a non-steroidal anti-inflammatory drug (NSAID) selected from the group consisting of a salt of naproxen, diclofenac, ibuprofen, and combinations thereof; and
a pharmaceutically acceptable anionic surfactant selected from the group consisting of sodium lauryl sulfate, docusate sodium, docusate calcium, and combinations thereof;
wherein the opioid, the salt of an NSAID, and the anionic surfactant are within the hydrophilic matrix.

56. The composition of embodiment 55 which exhibits a release profile comprising a substantial portion that is representative of zero-order release kinetics under in vitro conditions.

57. The composition of embodiment 55 or embodiment 56 wherein the opioid is selected from the group consisting of hydrocodone, a salt thereof, and combinations thereof.

58. The composition of embodiment 57 wherein the opioid comprises hydrocodone bitartrate.

59. The composition of embodiment 55 or embodiment 56 wherein the opioid is selected from the group consisting of tramadol, a salt thereof, and combinations thereof.

60. The composition of embodiment 59 wherein the opioid comprises tramadol hydrochloride.

61. The composition of any one of embodiments 55 through 60 wherein the pharmaceutically acceptable anionic surfactant is docusate sodium.

62. The composition of any one of embodiments 55 through 61 wherein the hydrophilic polymeric compound comprises a cellulose ether.

63. The composition of embodiment 62 wherein the cellulose ether comprises a hydroxyalkyl cellulose, a carboxyalkyl cellulose, and combinations thereof.

64. The composition of embodiment 63 wherein the cellulose ether comprises a methylcellulose, a hydroxypropyl methylcellulose, and combinations thereof.

65. The composition of embodiment 64 wherein the cellulose ether comprises a hydroxypropyl methylcellulose.

66. A sustained-release oral pharmaceutical composition comprising within a single dosage form:
a hydrophilic matrix comprising a hydroxypropyl methylcellulose;
a therapeutically effective amount of an opioid selected from the group consisting of hydrocodone, a salt thereof, and combinations thereof;
a salt of a non-steroidal anti-inflammatory drug (NSAID) selected from the group consisting of a salt of naproxen, and combinations thereof; and
a pharmaceutically acceptable anionic surfactant selected from the group consisting of docusate sodium, docusate calcium, and combinations thereof;
wherein the opioid, the salt of an NSAID, and the anionic surfactant are within the hydrophilic matrix.

67. A sustained-release oral pharmaceutical composition comprising within a single dosage form:
a hydrophilic matrix comprising a hydroxypropyl methylcellulose;
a therapeutically effective amount of an opioid selected from the group consisting of tramadol, a salt thereof, and combinations thereof;

a salt of a non-steroidal anti-inflammatory drug (NSAID) selected from the group consisting of a salt of naproxen, and combinations thereof; and
a pharmaceutically acceptable anionic surfactant selected from the group consisting of docusate sodium, docusate calcium, and combinations thereof;
wherein the opioid, the salt of an NSAID, and the anionic surfactant are within the hydrophilic matrix.

68. The composition of embodiment 66 or embodiment 67 which exhibits a release profile comprising a substantial portion that is representative of zero-order release kinetics under in vitro conditions.

69. A method of preventing, alleviating, or ameliorating the level of pain in a subject, the method comprising administering to a subject a composition of any one of embodiments 1 through 68.

70. A method of suppressing cough in a subject, the method comprising administering to a subject a composition of any one of embodiments 1 through 68.

71. A method of preventing, alleviating, or ameliorating the level of pain in a subject, the method administering to a subject a composition comprising:
a hydrophilic matrix;
a pain-reducing amount of an opioid analgesic (including salts thereof); and
a salt of a non-steroidal anti-inflammatory drug (NSAID) present in an amount effective to provide zero-order release kinetics under in vitro conditions;
wherein the opioid analgesic and the salt of an NSAID are within the hydrophilic matrix; and
wherein the composition has a release profile comprising a substantial portion that is representative of zero-order release kinetics under in vitro conditions.

72. A method of preventing, alleviating, or ameliorating the level of pain in a subject, the method administering to a subject a composition comprising:
a hydrophilic matrix;
a therapeutically effective amount of an opioid analgesic (including salts thereof);
a salt of a non-steroidal anti-inflammatory drug (NSAID); and
a pharmaceutically acceptable anionic surfactant;
wherein the opioid analgesic, the salt of an NSAID, and the anionic surfactant are within the hydrophilic matrix.

73. The method of embodiment 72 which has a release profile comprising a substantial portion that is representative of zero-order release kinetics under in vitro conditions.

74. The method of any one of embodiments 69 through 73 wherein administering the composition comprises administering once or twice per day.

75. The method of embodiment 74 wherein administering the composition comprises administering once per day.

EXAMPLES

Objects and advantages of this invention are further illustrated by the following examples, but the particular materials and amounts thereof recited in these examples, as well as other conditions and details, should not be construed to unduly limit this invention.

Example 1

Preparation of Sustained-Release Hydrophilic Matrix Tablets Containing Tramadol Hydrochloride (TMD), Naproxen Sodium (NAP), and Docusate Sodium (DSS) at Benchtop Scale Each hydrophilic matrix tablet lot was produced by dry-blending the active substance(s) and excipients together followed by direct compression. The TMD and NAP (when present) were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. Lots without NAP were compressed using 0.3125-inch round, concave Natoli tooling (HOB No. 91300), while lots containing NAP were compressed using 0.3750-inch round, concave Natoli tooling (HOB No. 91380). The compression force was varied until a tablet breaking force of 14-16 kPa was consistently achieved.

TABLE 1

Prototype formulation compositions (mg/tablet)

| Lot No. | Tramadol Hydrochloride (Spectrum Chemical Manufacturing Corp.) | Methocel K4M (Dow Chemical) | Avicel PH-302 (FMC Biopolymer) | Naproxen Sodium (Albemarle Corp.) | Granular Docusate Sodium (Cytec Industries, Inc.) | Total Tablet Mass (mg) |
|---|---|---|---|---|---|---|
| Prototype 1 | 15.0 | 120.0 | 45.0 | | | 180.0 |
| Prototype 2 | 15.0 | 120.0 | 45.0 | | 17.6 | 197.6 |
| Prototype 3 | 15.0 | 120.0 | 45.0 | | 117.7 | 297.7 |
| Prototype 4 | 15.0 | 120.0 | 45.0 | 220.0 | | 400.0 |
| Prototype 5 | 15.0 | 120.0 | 45.0 | 220.0 | 8.8 | 408.8 |
| Prototype 6 | 15.0 | 120.0 | 45.0 | 220.0 | 17.6 | 417.6 |
| Prototype 7 | 15.0 | 120.0 | 45.0 | 220.0 | 29.4 | 429.4 |
| Prototype 8 | 15.0 | 120.0 | 45.0 | 220.0 | 117.7 | 517.7 |

USP Apparatus 2 was used for the dissolution testing of the prototype tablets produced. The dissolution samples were assayed for TMD using HPLC with UV detection at 280 nm. The system parameters for both the chromatographic and dissolution analysis are shown below.
System: Hewlett Packard 1100 Series HPLC System
Column: Phenomenex Jupiter C18, 250×4.6 mm ID, 5μ, 300 Å Part No.: 000-4053-EO
Detector: UV detector, 280 nm
Mobile Phase A: 94.7/5.0/0.3 (v/v/v) water/methanol/TFA
Mobile Phase B: Pure methanol
Method Type Gradient
Flow Rate: 1.5 mL/min
Injection Volume: 30 μL Run Time: 8.00 minutes (8.01-10.00 minutes is reequilibration)
Peakwidth: >0.1 min
Column Temp.: 35° C.
Autosampler Temp.: Ambient

TABLE 2

Gradient profile for HPLC mobile phases A and B

| Initial | 60% A | 40% B |
| 8.00 | 10% A | 90% B |
| 8.01 | 60% A | 40% B |
| 10.00 | 60% A | 40% B |

TABLE 3

Dissolution parameters

| Parameters | Requirements |
| --- | --- |
| Method Type | USP Apparatus 2 (Paddle Method) |
| Rotation Speed | 50 rpm |
| Dissolution Media | pH 7.5 phosphate buffer (0.05 M, potassium phosphate monobasic 0.68%/NaOH 0.164%) |
| Media Volume | 900 mL |
| Media Temperature | 37.0 ± 0.5° C. |
| Sampling Time Points | 1, 3, 6, 9 and 12 hours |
| Sampling Volume | 10 mL without media replacement (Use 10 μm Full-flow Filter) |

FIG. 1 illustrates zero-order release kinetics over 12 hours for TMD from the hydrophilic matrix containing naproxen sodium with and without docusate sodium. Prototype 4 contains no DSS, indicating that the surfactant is not critical to achieving linear release kinetics. Prototypes 5-8 reveal that the addition of surfactant into the hydrophilic matrix does impact the rate and extent of release, with higher DSS levels showing a slower release rate and a lower extent of release at 12 hours. Regardless of DSS level, all dissolution profiles in the presence of naproxen sodium are zero-order.

To further illustrate the importance of naproxen sodium and DSS to the release kinetics of TMD from the hydrophilic matrix, FIG. 2 shows dissolution profiles for several formulations in which key components have been added or removed. Prototype 1 shows the release of TMD from the hydrophilic matrix in the absence of naproxen sodium and DSS. This formulation shows the largest extent of release, however, the release profile is non-linear, indicating that zero-order release is not achieved. Prototypes 2 and 3 show the release profile of TMD at increasing levels of DSS (15 and 100 mg, respectively), revealing that surfactant level can also be used to control the rate and extent of TMD release when the NSAID salt is absent from the hydrophilic matrix. Prototypes 6 and 8 show TMD release profiles at the same two DSS concentrations (15 and 100 mg, respectively) in the presence of naproxen sodium. Here, the addition of the NSAID salt to the matrix increases the rate and extent of TMD release, while also causing the release rate to become zero-order.

Example 2

Preparation of Sustained-Release Hydrophilic Matrix Tablets Containing Hydrocodone Bitartrate (HCB), Naproxen Sodium (NAP), and Docusate Sodium (DSS) at Benchtop Scale Each hydrophilic matrix tablet lot was produced by dry-blending the active substance(s) and excipients together followed by direct compression. The blending process involved two steps. The HCB and NAP (when present) were blended together with all excipients except the Methocel K4M Premium which was later added and blended during the second step. Blending was accomplished by first dispensing the powdered components into a stainless steel pan. The components were then mixed together using a stainless steel spatula to affect homogenization of the blend. After approximately 2-3 minutes of mixing, the powders were transferred to a stainless steel 40 mesh screen where they were pushed through using a plastic sieve scraper. The pass through was collected in a separate stainless steel pan. The mixing and sieving processes were then repeated. Each blending step required two mixing and two sieving processes. After the final step, the dry blend was transferred to a HDPE bag. Aliquots of the blend were massed out using an analytical balance and were compressed using a GlobePharma MTCM-1 hand tablet press. Lots without NAP were compressed using 0.3125-inch round, concave Natoli tooling (HOB No. 91300), while lots containing NAP were compressed using 0.3750-inch round, concave Natoli tooling (HOB No. 91380). The compression force was varied until a tablet breaking force of 14-16 kPa was consistently achieved.

TABLE 4

Prototype formulation compositions (mg/tablet)

| Lot No. | Hydrocodone Bitartrate (Mallinckrodt) | Methocel K4M (Dow Chemical) | Avicel PH-302 (FMC Biopolymer) | Naproxen Sodium (Albemarle Corp.) | Granular Docusate Sodium (Cytec Industries, Inc.) | Total Tablet Mass (mg) |
| --- | --- | --- | --- | --- | --- | --- |
| Prototype 1 | 15.0 | 120.0 | 45.0 | | | 180.0 |
| Prototype 2 | 15.0 | 120.0 | 45.0 | | 17.6 | 197.6 |
| Prototype 3 | 15.0 | 120.0 | 45.0 | | 117.7 | 297.7 |
| Prototype 4 | 15.0 | 120.0 | 45.0 | 220.0 | | 400.0 |
| Prototype 5 | 15.0 | 120.0 | 45.0 | 220.0 | 8.8 | 408.8 |
| Prototype 6 | 15.0 | 120.0 | 45.0 | 220.0 | 17.6 | 417.6 |
| Prototype 7 | 15.0 | 120.0 | 45.0 | 220.0 | 29.4 | 429.4 |
| Prototype 8 | 15.0 | 120.0 | 45.0 | 220.0 | 117.7 | 517.7 |

USP Apparatus 2 was used for the dissolution testing of the prototype tablets produced. The dissolution samples were assayed for HCB using HPLC with UV detection at 280 nm.

The system parameters for both the chromatographic and dissolution analysis are shown below.

System: Waters Alliance 2487 HPLC System
Column: Phenomenex Jupiter C18, 250×4.6 mm ID, 5μ, 300 Å Part No.: 00G-4053-EO
Detector: UV detector, 280 nm
Mobile Phase A: 94.7/5.0/0.3 (v/v/v) water/methanol/TFA
Mobile Phase B: Pure methanol
Method Type Gradient
Flow Rate: 1.5 mL/min
Injection Volume: 30 μL
Run Time: 11 minutes (11.01-13.00 minutes is reequilibration)
Peakwidth: >0.1 min
Column Temp.: 35° C.
Autosampler Temp.: Ambient

TABLE 5

Gradient profile for HPLC mobile phases A and B

| Initial | 90% A | 10% B |
|---|---|---|
| 10.00 | 10% A | 90% B |
| 11.00 | 10% A | 90% B |
| 11.01 | 90% A | 10% B |
| 13.00 | 90% A | 10% B |

TABLE 6

Dissolution parameters

| Parameters | Requirements |
|---|---|
| Method Type | USP Apparatus 2 (Paddle Method) |
| Rotation Speed | 50 rpm |
| Dissolution Media | pH 7.5 phosphate buffer (0.05 M, potassium phosphate monobasic 0.68%/NaOH 0.164%) |
| Media Volume | 900 mL |
| Media Temperature | 37.0 ± 0.5° C. |
| Sampling Time Points | 1, 3, 6, 9 and 12 hours |
| Sampling Volume | 3 mL without media replacement (Use 10 μm Full-flow Filter) |

FIG. 3 illustrates zero-order release kinetics over 12 hours for HCB from the hydrophilic matrix containing naproxen sodium with and without docusate sodium. Prototype 4 contains no DSS, indicating that the surfactant is not critical to achieving linear release kinetics. Prototypes 5-8 reveal that the addition of surfactant into the hydrophilic matrix does impact the rate and extent of release, however, the rate and extent of release do not trend with surfactant level (as was observed for the TMD examples). The HCB tablets were compressed using a single-station press, making it difficult to control the dwell time. As a result, large variations in tablet hardness were observed (10-18 kP) for identical compression forces. It is hypothesized that this variation in tablet hardness could impact water uptake and swelling rates, resulting in the hysteresis observed in FIG. 3. Regardless of DSS level, all dissolution profiles in the presence of naproxen sodium are zero-order.

To further illustrate the importance of naproxen sodium and DSS to the release kinetics of HCB from the hydrophilic matrix, FIG. 4 shows dissolution profiles for several formulations in which key components have been added or removed. Prototype 1 shows the release of HCB from the hydrophilic matrix in the absence of naproxen sodium and DSS. This formulation shows the largest extent of release, however, the release profile is non-linear, indicating that zero-order release is not achieved. Prototypes 2 and 3 show the release profile of HCB at increasing levels of DSS (15 and 100 mg, respectively), revealing that surfactant level can also be used to control the rate and extent of HCB release when the NSAID salt is absent from the hydrophilic matrix. Prototypes 6 and 8 show HCB release profiles at the same two DSS concentrations (15 and 100 mg, respectively) in the presence of naproxen sodium. Here, the addition of the NSAID salt to the matrix increases the rate and extent of HCB release, while also causing the release rate to become zero-order.

Example 3

Demonstration of the Abuse-Deterrent Features of Prototype Formulations Containing Dextromethorphan Hydrobromide (DXM), Naproxen Sodium (NAP) and Docusate Sodium (DSS)

Dose-Dumping

The abuse-deterrent characteristics of matrix tablets containing dextromethorphan hydrobromide (DXM) (used herein as an opioid surrogate), naproxen sodium (NAP), and docusate sodium (DSS) was demonstrated by performing hydroalcoholic in vitro dissolution and an independent small-volume extraction experiment.

DXM was chosen as an opioid surrogate due to its chemical, physical, and structural similarities to the opioid analgesics useful in the practice of the present invention.

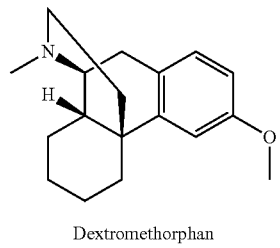

Dextromethorphan

NAP and DSS were selected because these two compounds represent a suitable NSAID salt and anionic surfactant, respectively, in the practice of the present invention.

The hydroalcoholic "dose dumping" experiment investigates the in vitro opioid (or opioid surrogate) release behavior in the presence of alcohol. The experiment models ingestion of a tablet with the concomitant use of alcoholic beverages (i.e., ethanol).

Each hydrophilic matrix tablet lot was produced by dry-blending the active substance(s) and excipients together followed by direct compression. The DXM and NAP were added together with all excipients in an HDPE bag. Blending was accomplished by manually mixing the contents of the bag for five minutes. Aliquots of the blend were massed out using an analytical balance and were compressed using a Manesty DC16 press. Each tablet aliquot was added to the die manually and compressed at a speed of 5 rpm. Prototypes 1, 2, and 3 were compressed using 0.3750 in. round, concave Natoli tooling (HOB #91380). The compression force was varied until a tablet breaking force of 14-16 kPa was consistently achieved.

TABLE 7

Prototype formulation compositions (mg/tablet)

| Lot No. | Dextromethorphan Hydrobromide (Wockhardt Limited) | Methocel K4M (Dow Chemical) | Avicel PH-302 (FMC Biopolymer) | Naproxen Sodium (Albemarle Corp.) | Granular Docusate Sodium (Cytec Industries, Inc.) | Total Tablet Mass (mg) |
|---|---|---|---|---|---|---|
| Prototype 1 | 15.0 | 120.0 | 45.0 | 220.0 | 17.6 | 417.6 |
| Prototype 2 | 15.0 | 120.0 | 45.0 | 220.0 | 29.4 | 429.4 |
| Prototype 3 | 15.0 | 120.0 | 45.0 | 220.0 | 58.8 | 458.8 |

In order to assess the potential for "dose dumping," the dissolution method was modified by changing the media to 0.1N HCl with varying levels of alcohol (ethanol). USP Apparatus 2 was used for the dissolution testing of the prototype tablets. The dissolution samples were assayed for DXM using HPLC with UV detection at 280 nm. The system parameters for both the chromatographic and dissolution analysis are shown below.
System: Agilent 1100 series HPLC system
Column: Phenomenex Jupiter C18, 250×4.6 mm ID, 5μ, 300 Å Part No.: 00G-4053-EO
Detector: UV detector, 280 nm
Mobile Phase A: 94.7/5.0/0.3 (v/v/v) water/methanol/TFA
Mobile Phase B: Pure methanol
Method Type Gradient
Flow Rate: 1.5 mL/min
Injection Volume: 30 μL
Run Time: 8.00 minutes (8.01-10.00 minutes is reequilibration)
Peakwidth: >0.1 min
Column Temperature: 35° C.
Autosampler temp: Ambient

TABLE 8

Gradient profile for HPLC mobile phases A and B

| Initial | 60% A | 40% B |
|---|---|---|
| 8.00 | 10% A | 90% B |
| 8.01 | 60% A | 40% B |
| 10.00 | 60% A | 40% B |

TABLE 9

Dissolution parameters

| Parameters | Requirements |
|---|---|
| Method Type | USP Apparatus 2 (Paddle Method) |
| Rotation Speed | 50 rpm |
| Dissolution Media | pH 1.2 USP buffer |
| | pH 1.2 USP buffer (5% ethanol) |
| | pH 1.2 USP buffer (20% ethanol) |
| Media Volume | 900 mL |
| Media Temperature | 37.0 ± 0.5° C. |
| Sampling Time Points | 1, 3, 6, 9 and 12 hours |
| Sampling Volume | 8 mL without media replacement (Use 10 μm Full-flow Filter) |

The purpose of this investigation was to measure the integrity of the dosage formulation using acidic, hydroalcoholic dissolution media. For this experiment, intact tablets were evaluated. Prototype 1 was evaluated since this formulation is expected to show significantly greater DXM release over 12 hours compared to Prototypes 2 and 3 based on evaluation of previous formulations of similar composition.

Dissolution profiles are provided in FIG. 5. The results demonstrate that "dose dumping" does not occur, even with a 20% ethanol level in the dissolution media. In addition, zero-order release is maintained from 0-20% ethanol Opioid Extraction The small-volume extraction experiment models the attempted extraction of opioid that a substance abuser might undertake. In this experiment, tablets were crushed and extracted with two common solvents, water and 40% alcohol. A single tablet was crushed and stirred with a small volume of solvent (50 mL). At time points of 30 minutes and 12 hours, aliquots were removed and assayed for both DXM and docusate. Prior to HPLC analysis the aliquots were filtered using a 10 μm full-flow filter and subsequently centrifuged at 1000 rpm for 30 minutes. The supernatant from this procedure was filled directly into HPLC vials for analysis. The HPLC assay for DXM has been described previously. The following HPLC method was developed to assay docusate:
System: Agilent 1100 series HPLC system
Column: YMC-Pack CN, 250 mm×4.6 mm ID, 5μ, 120 Å Part number: CN12S052546WT
Detector: UV detector, 225 nm
Mobile Phase A: 0.02M tetrabutylammonium hydrogen sulfate
Mobile Phase B: Pure acetonitrile
Method Type Isocratic 40% A/60% B
Flow Rate: 1.5 mL/min
Injection Volume: 10 μL
Run Time: 5 minutes
Peakwidth: >0.1 min
Column Temperature: 45° C.
Autosampler temp: Ambient

TABLE 10

Simultaneous Release of Dextromethorphan Hydrobromide and Docusate Sodium From Crushed Tablets to Assess Abuse Potential

| Formulation | Extraction Solvent | DXM Released in 30 minutes | Docusate Released in 30 minutes | DXM Released in 12 hours | Docusate Released in 12 hours |
|---|---|---|---|---|---|
| Prototype 1 | Water | 58% | 80% | 47% | 61% |
| Prototype 1 | Alcohol 40% | 93% | 91% | 100% | 98% |
| Prototype 2 | Water | 35% | 47% | 35% | 47% |
| Prototype 2 | Alcohol 40% | 95% | 93% | 114% | 108% |
| Prototype 3 | Water | 52% | 48% | 50% | 43% |

TABLE 10-continued

Simultaneous Release of
Dextromethorphan Hydrobromide and Docusate
Sodium From Crushed Tablets to Assess Abuse Potential

| Formulation | Extraction Solvent | DXM Released in 30 minutes | Docusate Released in 30 minutes | DXM Released in 12 hours | Docusate Released in 12 hours |
|---|---|---|---|---|---|
| Prototype 3 | Alcohol 40% | 68% | 67% | 102% | 95% |

The data (Table 10) demonstrates the simultaneous release of DXM and docusate from formulations containing different levels of docusate (Table 7). This data shows that extraction and separation of DXM and docusate from these formulations would require advanced chemical knowledge and substantial effort, and would likely be time-consuming. The commingling of DXM and docusate would make injection of extracted solutions unattractive to an abuser, and potentially harmful. Additionally, drying the solution to create a solid would be of no benefit to a drug abuser, as the solid would be impure and contain irritating docusate. It is expected that similar results would be obtained for formulations according to the present invention that comprise an opioid analgesic.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. A sustained-release oral pharmaceutical composition comprising within a single dosage form:
    a hydrophilic matrix;
    a therapeutically effective amount of an opioid selected from the group consisting of hydrocodone, tramadol, salts thereof, and combinations thereof;
    a salt of a non-steroidal anti-inflammatory drug (NSAID) selected from the group consisting of a salt of naproxen, diclofenac, ibuprofen, and combinations thereof; and
    a pharmaceutically acceptable anionic surfactant selected from the group consisting of sodium lauryl sulfate, docusate sodium, docusate calcium, and combinations thereof;
    wherein the opioid, the salt of an NSAID, and the anionic surfactant are within the hydrophilic matrix.

2. The composition of claim 1 which exhibits a release profile with respect to the opioid comprising a substantial portion that is representative of zero-order release kinetics under in vitro conditions.

3. The composition of claim 1 wherein the opioid is selected from the group consisting of hydrocodone, a salt thereof, and combinations thereof.

4. The composition of claim 3 wherein the opioid comprises hydrocodone bitartrate.

5. The composition of claim 1 wherein the opioid is selected from the group consisting of tramadol, a salt thereof, and combinations thereof.

6. The composition of claim 5 wherein the opioid comprises tramadol hydrochloride.

7. The composition of claim 1 wherein the pharmaceutically acceptable anionic surfactant is docusate sodium.

8. The composition of claim 1 wherein the matrix comprises a cellulose ether.

9. The composition of claim 8 wherein the cellulose ether comprises a hydroxyalkyl cellulose, a carboxyalkyl cellulose, and combinations thereof.

10. The composition of claim 1 wherein the matrix comprises a methylcellulose, a hydroxypropyl methylcellulose, and combinations thereof.

11. The composition of claim 1 wherein the matrix comprises a hydroxypropyl methylcellulose.

12. A sustained-release oral pharmaceutical composition comprising within a single dosage form:
    a hydrophilic matrix comprising a hydroxypropyl methylcellulose;
    a therapeutically effective amount of an opioid selected from the group consisting of hydrocodone, a salt thereof, and combinations thereof;
    a salt of a non-steroidal anti-inflammatory drug (NSAID) selected from the group consisting of a salt of naproxen, and combinations thereof; and
    a pharmaceutically acceptable anionic surfactant selected from the group consisting of docusate sodium, docusate calcium, and combinations thereof;
    wherein the opioid, the salt of an NSAID, and the anionic surfactant are within the hydrophilic matrix.

13. The composition of claim 12 which exhibits a release profile with respect to the opioid comprising a substantial portion that is representative of zero-order release kinetics under in vitro conditions.

14. The composition of claim 12 wherein the opioid comprises hydrocodone bitartrate.

15. The composition of claim 12 wherein the pharmaceutically acceptable anionic surfactant is docusate sodium.

16. The composition of claim 12 wherein the salt of an NSAID comprises naproxen sodium.

17. A sustained-release oral pharmaceutical composition comprising within a single dosage form:
    a hydrophilic matrix comprising a hydroxypropyl methylcellulose;
    a therapeutically effective amount of an opioid selected from the group consisting of tramadol, a salt thereof, and combinations thereof;
    a salt of a non-steroidal anti-inflammatory drug (NSAID) selected from the group consisting of a salt of naproxen, and combinations thereof; and
    a pharmaceutically acceptable anionic surfactant selected from the group consisting of docusate sodium, docusate calcium, and combinations thereof;
    wherein the opioid, the salt of an NSAID, and the anionic surfactant are within the hydrophilic matrix.

18. The composition of claim 17 which exhibits a release profile with respect to the opioid comprising a substantial portion that is representative of zero-order release kinetics under in vitro conditions.

19. The composition of claim 17 wherein the opioid comprises tramadol hydrochloride.

20. The composition of claim 17 wherein the pharmaceutically acceptable anionic surfactant is docusate sodium.

* * * * *